United States Patent [19]
Lesieur et al.

[11] Patent Number: 5,919,784
[45] Date of Patent: Jul. 6, 1999

[54] HETEROCYCLIC AMINOMETHYL COMPOUNDS

[75] Inventors: Daniel Lesieur, Gondecourt; Pascal Carato, Commentry; Jean-Paul Bonte, Wasquehal; Patrick Depreux, Armentieres; Daniel-Henri Caignard, Le Pecq; Mark Millan, Le Pecq; Adrian Newman-Tancredi, Le Pecq; Pierre Renard, Versailles; Marie-Claire Rettori, Courbevoie, all of France

[73] Assignee: Adir Et Compagnie, Courbevoie, France

[21] Appl. No.: 08/966,040

[22] Filed: Nov. 7, 1997

[30] Foreign Application Priority Data

Nov. 8, 1996 [FR] France ................................ 9613652

[51] Int. Cl.$^6$ ...................... A61K 413/10; A61K 417/10; C07D 31/495; C07D 31/535
[52] U.S. Cl. ............................ 514/253; 544/52; 544/105; 544/364; 544/368; 544/295; 546/187; 546/201; 514/224.2; 514/230.5; 514/316; 514/323; 514/256
[58] Field of Search .................................... 544/364, 368, 544/295; 514/253

[56] References Cited

U.S. PATENT DOCUMENTS 4,960,778  10/1990  Lesieur et al. .......................... 514/253
5,234,924   8/1993  Taverne et al. ....................... 514/224.2

OTHER PUBLICATIONS

Marzella et al., "The Binding of Both[$^3$H] Nemonapride and . . . ", Society of Biological Psychiatry, 1997, 42 8, 648.
Meador–Woodruff et al., "Dopamine Receptor Transcript Expression . . . ", Arch. Gen. Psyciatry, 1997, 54, 12, 1089.
Rubenstein et al., "Mice Lacking Dopamine D4 Receptors . . . ", Cell., 1997, 90, 6.
Reynolds, "The Importance of Dopamine D4 Receptors in the Action and Development of Antipsychotic Agents," Drugs, vol. 51, No. 1, pp. 7–11, 1996.
Kulagowski et al., "Dopamine D4 Receptor Antagonists," Current Pharmaceutical Design, vol. 3, pp. 355–366, 1997.
Manki et al., "Dopamine D2, D3 and D4 Receptor and Transporter Gene Polymorphisms and Mood Disorders," Journal of Affective Disorders, vol. 40, pp. 7–13, 1996.

*Primary Examiner*—Mukund J. Shah
*Assistant Examiner*—Ann M. Kessinger
*Attorney, Agent, or Firm*—The Firm of Gordon W. Hueschen

[57] ABSTRACT

A compound of general formula (I):

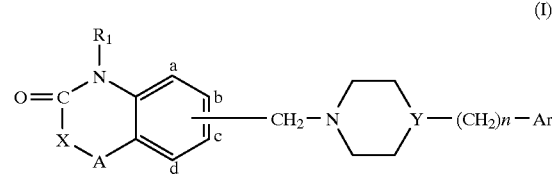

where A, X, $R_1$, Y, n and Ar are defined in the description. Medicinal products containing the same are useful as $D_4$ receptor Ligands.

9 Claims, No Drawings

HETEROCYCLIC AMINOMETHYL COMPOUNDS

TITLE OF THE INVENTION

The present invention relates to new heterocyclic aminomethyl compounds.

DESCRIPTION OF THE PRIOR ART

Numerous heterocyclic alkylamines containing a benzoxazolinone, benzothiazolinone or benzoxazinone moiety have already been described.

European Patent EP 0 110781 describes 6-(2-aminoethyl) benzoxazolinones as hypnotics and agents for the treatment of cardiac insufficiency. European Patent Application EP 0 281 309 describes compounds of piperazinoethyl- or -butylbenzoxazolinone and -benzothiazolinone structure which are useful as antipsychotics.

French Patent FR 2035749 describes aminoalkylbenzoxazinones which are useful for the treatment of central nervous system disorders.

The publication "Il farmaco" 89, 44 (1), 77–88 describes arylpiperazinobutylbenzoxazolinones as well as their essentially analgesic properties.

Patent Application EP 0 223674 describes 7-acylbenzoxazinones and their derivatives as possessing antiatherosclerotic and normolipemic properties.

Patent Application EP 0 478446 describes heterocyclic ethyl- and butylamines which possess the property of binding with very high affinity to the 5-$HT_{1A}$ serotoninergic receptors.

BACKGROUND OF THE INVENTION

The Applicant has now discovered new heterocyclic aminomethyl compounds, more especially aminomethylbenzoxazolinone, -benzothiazolinone and -benzoxazinone compounds, which, contrary to the compounds of the prior art and most surprisingly, no longer have other than a weak affinity for the 5-$HT_{1A}$ and $D_2$ receptors. At the same time, these new compounds possess excellent affinity for the $D_4$ receptors, whereas a comparison carried out on the compounds mentioned in the documents of the prior art established, in effect, that the latter compounds had no affinity for these $D_4$ receptors.

The $D_4$ receptors are localized in the corticolimbic structures (frontal cortex, nucleus accumbens and hippocampus) involved in the control of mood and memory (Bloom and Kupfer, in Psychopharmacology "The fourth generation of progress" Raven Press, New York 1995; Meador-Woodruff et al., "Dopamine receptor mRNA expression in human striatum and neocortex". Neuropsychopharmacology, 1996; 15:17–29). In these structures, a subpopulation is localized on the GABAergic type neurons, which also play a key part in the modulation of mood and of the cognitive functions (Bloom and Kupfer, 1995 (already cited)); Mrzkjak et al., "Localisation of dopamine $D_4$ receptors in GABAergic neurons of the primate brain". Nature, 1996; 381:245–248). Some studies have shown an increase in the density of the $D_4$ receptors in psychotic patients, while clozapine shows a high affinity for the $D_4$ receptors (Van Tol et al., "Cloning of the gene for a human dopamine $D_4$ receptor with high affinity for the antipsychotic clozapine". Nature, 1991; 350:610–614). In addition, noradrenaline, a neurotransmitter involved in psychotic, anxiety and depressive states as well as cognitive and attention disorders (Bloom and Kupfer, 1995 (already cited)), possesses a high affinity for the $D_4$ receptors (Lanau et al., "Epinephrine and norepinephrine act as potent agonists at the human recombinant $D_{4.4}$ receptor". Am. Soc. Neurosci., 1995; 21:252.2). These results demonstrate the value of the products of the invention in the treatment of schizophrenia, anxiety, depression, drug abuse, impulsive states (e.g. aggressiveness) and mnemocognitive disorders. Furthermore, the high concentration of $D_4$ receptors in the superficial layer of the spinal cord (Matsumoto et al., "Low levels of mRNA for dopamine $D_4$ receptor in human cerebral cortex and striatum". J. Neurochem., 1996; 66: 915–919) suggests a value in the treatment of painful (e.g. neuropathic or migrainous) states.

DETAILED DESCRIPTION OF THE INVENTION

More specifically, the present invention relates to the compounds of general formula (I):

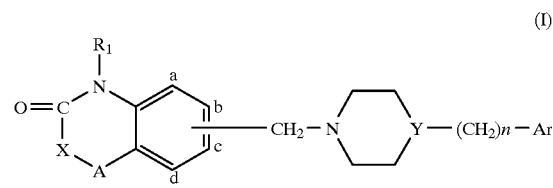

in which:
$R_1$ represents a hydrogen atom or a lower alkyl group, or alternatively
$R_1$ represents a group

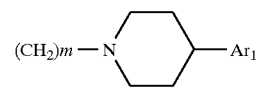

in which m represents an integer between 1 and 4 inclusive and $Ar_1$ represents
either a group CO—$Ar_2$ where $Ar_2$ represents a phenyl ring unsubstituted or substituted with one or more radicals chosen from halogen, hydroxyl, lower alkyl, trifluoromethyl or lower alkoxy,
or a group =C—$(Ar_2)_2$ where $Ar_2$ has the same meaning as above,
n represents 0 or 1
A represents an oxygen or sulfur atom
X represents a $CH_2$ group or a single bond
Y represents a CH group or a nitrogen atom
Ar represents a phenyl or naphthyl group optionally substituted with one, two or three groups chosen from halogen, hydroxyl, lower alkoxy, lower alkyl, (lower alkoxy)(lower alkyl), trifluoromethyl or aminosulfonyl, or Ar represents a pyridyl or pyrimidinyl group or a 3-(benzo[d]1,2-thiazolyl) group also known as a 3-benzisothiazolyl group:

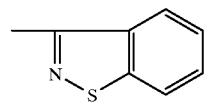

where appropriate their isomers, pure or mixed, as well as their addition salts with a pharmaceutically acceptable acid, or a pharmaceutically acceptable base when $R_1$=H on the understanding that, except where otherwise stated, the terms "lower alkyl" and "lower alkoxy" correspond to linear or branched groups containing from 1 to 6 carbon atoms.

Among pharmaceutically acceptable acids, there may be mentioned, without implied limitation, hydrochloric, sulfuric, tartaric, maleic, fumaric, oxalic, methanesulfonic, camphoric, ethanesulfonic, citric, and the like, acids.

Among pharmaceutically acceptable bases, there may be mentioned, without implied limitation, sodium, potassium and calcium hydroxides as well as sodium, potassium, calcium, and the like, carbonates.

The invention relates preferentially to the compounds of formula (I) for which, taken together or separately:

$R_1$ is a hydrogen atom, a methyl group or a group $$(CH_2)_m-N\diagup\diagdown Ar_1$$

for which m equals 2 and $Ar_1$ represents either a $$CO-\bigcirc-F$$

group or alternatively a $$=C{\left(-\bigcirc-F\right)}_2$$

group

A is a sulfur atom and X represents a single bond; the compounds are then derivatives of benzoxazolinone of formula:

[structure]

A is an oxygen atom and X represents a single bond; the compounds are then derivatives of benzothiazolinone of formula

[structure]

A is an oxygen atom and X represents a $CH_2$ group; these compounds are derivatives of benzoxazinone of formula

[structure]

the side chain is grafted at position c n represents 0

Y represents a nitrogen atom

Ar represents a phenyl group substituted with a fluorine atom or alternatively with a chlorine atom or alternatively with a methoxy group, as well as their isomers, pure or mixed, as well as their addition salts with a pharmaceutically acceptable acid, or a pharmaceutically acceptable base when $R_1$ is a hydrogen atom.

Preferentially the invention relates to:

3-methyl-6-{[4-(2-methoxyphenyl)-1-piperazinyl] methyl}benzoxazolinone, as well as its addition salts with a pharmaceutically acceptable acid, 3-methyl-6-{[4-(2-methoxyphenyl)-1-piperazinyl] methyl}benzothiazolinone, as well as its addition salts with a pharmaceutically acceptable acid, 3-methyl-6-{[4-(2-fluorophenyl)-1-piperazinyl] methyl}benzothiazolinone, as well as its addition salts with a pharmaceutically acceptable acid, 4-methyl-7-{[4-(2-methoxyphenyl)-1 -piperazinyl]methyl}-3-oxo-3,4-dihydro-2H-1,4-benzoxazine, as well as its addition salts with a pharmaceutically acceptable acid, 3-methyl-6-{[4-(2-fluorophenyl)-1-piperazinyl] methyl}benzoxazolinone, as well as its addition salts with a pharmaceutically acceptable acid, 4-methyl-7-{[4-(2-fluorophenyl)-1 -piperazinyl]methyl}-3-oxo-3,4-dihydro-2H-1,4-benzoxazine, as well as its addition salts with a pharmaceutically acceptable acid, 3-methyl-6-{[4-(4-chlorophenyl)-1-piperazinyl] methyl}benzoxazolinone, as well as its addition salts with a pharmaceutically acceptable acid, 3-methyl-6-{[4-(4-chlorophenyl)-1-piperazinyl] methyl}benzothiazolinone, as well as its addition salts with a pharmaceutically acceptable acid, 6-{[4-(2-fluorophenyl)-1-piperazinyl] methyl}benzoxazolinone, as well as its addition salts with a pharmaceutically acceptable acid or base, 6-{[4-(2-fluorophenyl)-1-piperazinyl] methyl}benzothiazolinone, as well as its addition salts with a pharmaceutically acceptable acid or base, 4-methyl-7-{[4-(4-chlorophenyl)-1 -piperazinyl]methyl}-3-oxo-3,4-dihydro-2H-1,4 benzoxazine, as well as its addition salts with a pharmaceutically acceptable acid, 3-{2-[4-(4-fluorobenzoyl)-1-piperidyl]ethyl}-6-{[4-(2-fluorophenyl)-1-piperazinyl]methyl}benzoxazolinone, as well as its addition salts with a pharmaceutically acceptable acid, 3-{2-[4-(4',4'-difluorobenzhydrylidene)-1 -piperidyl]ethyl}-6-{[4-(2-fluorophenyl)-1-piperazinyl] methyl}benzoxazolinone, as well as its addition salts with a pharmaceutically acceptable acid, 3-{2-[4-(4-fluorobenzoyl)-1 -piperidyl]ethyl}-6-{[4-(2-fluorophenyl)-1-piperazinyl]methyl}-benzothiazolinone, as well as its addition salts with a pharmaceutically acceptable acid, 4-methyl-7-{[4-(benzo[d]-1,2-thiazolyl)-1 -piperazinyl] methyl}-3-oxo-3,4-dihydro-2H-1,4-benzoxazine, as well as its addition salts with a pharmaceutically acceptable acid, 3-methyl-6-{[4-(benzo[d]-1,2-thiazolyl)-1-piperazinyl]
methyl}benzoxazolinone, as well as its addition salts with
a pharmaceutically acceptable acid, 3-methyl-6-{[4-(benzo[d]-1,2-thiazolyl)-1-piperazinyl]
methyl}benzothiazolinone, as well as its addition salts
with a pharmaceutically acceptable acid, 3-methyl-6-{[4-(4-aminosulfonylphenyl)-1-piperazinyl]
methyl}benzoxazolinone, as well as its addition salts with
a pharmaceutically acceptable acid, 3-methyl-6-{[4-(4-aminosulfonylphenyl)-1-piperazinyl]
methyl}benzothiazolinone, as well as its addition salts
with a pharmaceutically acceptable acid, 4-methyl-7-{[4-(4-aminosulfonylphenyl)-1 -piperazinyl]
methyl}-3-oxo-3,4-dihydro-2H -1,4-benzoxazine, as well
as its addition salts with a pharmaceutically acceptable
acid, 3-methyl-6-{[4-(3-methoxyphenyl)-1-piperazinyl]
methyl}benzoxazolinone, as well as its addition salts with
a pharmaceutically acceptable acid, 4-methyl-7-{[4-(3-methoxyphenyl)-1 -piperazinyl]methyl}-
3-oxo-3,4-dihydro-2H-1,4 -benzoxazine, as well as its
addition salts with a pharmaceutically acceptable acid, 4-methyl-7-{[4-(4-methoxyphenyl)-1-piperazinyl]methyl}-
3-oxo-3,4-dihydro-2H-1,4-benzoxazine, as well as its
addition salts with a pharmaceutically acceptable acid, 3-methyl-6-{[4-(4-methoxyphenyl)-1-piperazinyl]
methyl}benzothiazolinone, as well as its addition salts
with a pharmaceutically acceptable acid, 3-methyl-6-{[4-(4-methoxyphenyl)-1-piperazinyl]
methyl}benzoxazolinone, as well as its addition salts with
a pharmaceutically acceptable acid.

The invention also extends to the process for preparing
the compounds of the formula (I), wherein on the one hand, when, in the compound of formula (I)
which it is desired to obtain, the group $R_1$ represents a
lower alkyl group, a compound of formula (II):

(II)

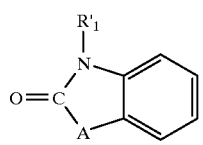

in which A has the same meaning as above and $R'_1$ represents a lower alkyl group is reacted with hexamethylenetetramine, preferably in an acid medium, to yield a product of formula (III):

(III)

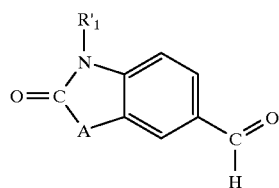

where $R'_1$ and A have the same meaning as above which is treated with a hydrogenating agent to yield a product of formula (IV):

(IV)

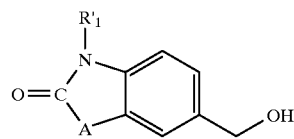

where $R'_1$ and A have the same meaning as above, on the other hand, when, in the compound of formula (I)
which it is desired to obtain, $R_1$ is other than a lower
alkyl group, a compound of formula (V):

(V)

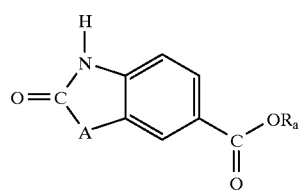

where $R_a$ represents a lower alkyl group and A has the same meaning as above, is treated with a hydrogenating agent to obtain a compound of formula (IVb):

(IVb)

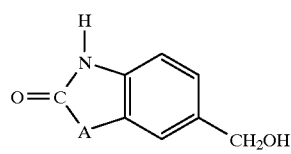

where A has the same meaning as above, which compound of formula (IV) or (IVb) is treated with
a halogenating agent to yield a product of formula (VI):

(VI)

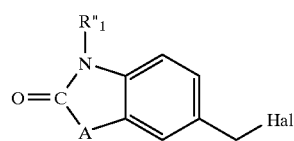

where $R''_1$ represents a hydrogen atom or a lower alkyl group and A has the same meaning as above and Hal represents a halogen atom which is treated with an amine of formula (VII):

(VII)

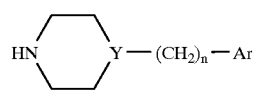

where Y, n and Ar have the same meaning as in the formula (I) to obtain a product of formula (I/a)

(I/a)

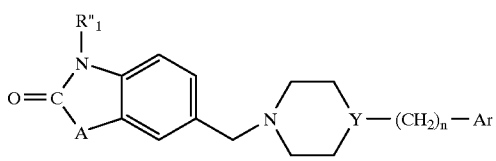

a special case of the compounds of formula (I) for which X represents a single bond, R"$_1$, A, Y, n and Ar having the same meaning as above which, when, in the product of formula (I) which it is desired to obtain, X represents a CH$_2$ group, is treated with an alkaline agent to yield a compound of formula (VIII):

(VIII)

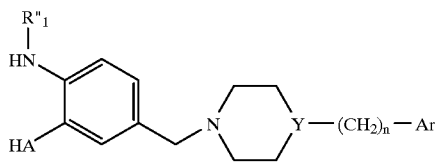

where A, R"$_1$, Y, Ar and n have the same meaning as above which compound of formula VIII is treated with ethyl bromoacetate in an alkaline medium to yield a product of formula (I/b):

(I/b)

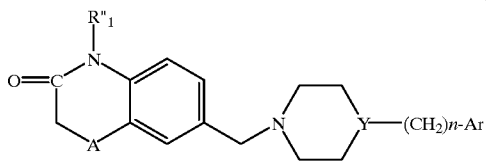

a special case of the compounds of formula (I) for which X represents a CH$_2$ group and R$_1$ a lower alkyl group or a hydrogen atom and Y and Ar have the same meaning as above, which compound of formula I/a or I/b is, when, in the compound of formula (I) which it is desired to obtain, R$_1$ represents neither a hydrogen atom nor a lower alkyl group, treated with a compound of formula (IX):

(IX)

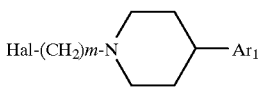

where Hal represents a halogen atom and m and Ar$_1$ have the same definition as in the formula (I) to yield a compound of formula I/c:

(I/c)

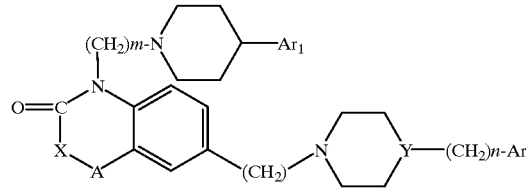

a special case of the compounds of formula (I) for which R$_1$ represents a group

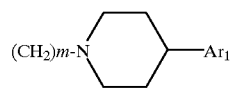

the compound of formula I/a, I/b or I/c thereby obtained being, where appropriate,
  purified by one or more methods chosen from crystallization, chromatography, extraction and passage through resin or charcoal
  separated, where appropriate, in pure form or in the form of a mixture, into its optical isomers,
  and, if so desired, salified with a pharmaceutically acceptable acid, or a pharmaceutically acceptable base.

The compounds of formula III, IV, IVb and VI are new and, as such, form part of the invention in the same way as the compounds of formula (I) for which they constitute synthesis intermediates, with the exception of the compound of formula III for which A represents an oxygen atom and R'$_1$ a methyl group (Renard et al.; Bull. Soc. Pharm. Lille, 1979, 2–3, 125–138). More especially, among these compounds, the following are preferred:
3-methyl-6-formylbenzothiazolinone,
3-methyl-6-(hydroxymethyl)benzoxazolinone,
3-methyl-6-(hydroxymethyl)benzothiazolinone,
6-(hydroxymethyl)benzoxazolinone,
6-(hydroxymethyl)benzothiazolinone,
the 3-methyl-6-(halomethyl)benzoxazolinones,
the 3-methyl-6-(halomethyl)benzothiazolinones,
the 6-(halomethyl)benzoxazolinones,
the 6-(halomethyl)benzothiazolinones.

The compounds of formula VIII are also new and also form part of the invention in the same way as the compounds of formula (I) for which they constitute synthesis intermediates, as well as their possible isomers and the addition salts with a pharmaceutically acceptable acid or base.

The compounds of formula (I) possess advantageous pharmacological properties.

Binding tests showed that the compounds of the invention behave as very potent D$_4$ receptor ligands. This affinity is accompanied by a very great selectivity with respect to the other receptors, in particular D$_2$. This is all the more surprising for the fact that the compounds of the prior art mentioned above do not have affinity for the D$_4$ receptor but possess, in contrast, a high affinity for the D$_2$ receptors.

The compounds of the invention are of low toxicity and, as a result of their receptor profile, should possess good activity in schizophrenia and in various categories of psychoses, in the modulation of mood and of the cognitive functions, in anxiety, depression, drug abuse, impulsive states and mnemocognitive disorders, as well as migrainous states.

The subject of the present invention is also pharmaceutical compositions containing as active principle at least one compound of general formula (I) or one of its addition salts with a pharmaceutically acceptable acid or, where appropriate, with a pharmaceutically acceptable base, alone or in combination with one or more inert, nontoxic excipients or vehicles.

Among the pharmaceutical compositions according to the invention, there may be mentioned, more especially, those which are suitable for oral, parenteral or nasal administration, simple or sugar-coated tablets, sublingual tablets, sachets, packets, hard gelatin capsules, preparations to be dissolved under the tongue, lozenges, suppositories, creams, ointments, skin gels, and the like.

The dosage varies according to the patient's age and weight, the nature and severity of the disorder and also the administration route. The latter can be oral, nasal, rectal or parenteral.

Generally speaking, the unit dosage ranges between 0.05 mg and 30 mg for disorders of mental behavior, in one to three doses per 24 hours.

The examples which follow illustrate the invention and in no way limit it.

$^1$H nuclear magnetic resonance spectra were carried out using TMS (tetramethylsilane) as internal reference. Chemical shifts are expressed in parts per million (ppm). Infrared spectra were recorded in the form of a potassium bromide disk containing approximately 1% of the product to be analyzed.

Except where otherwise stated, the preparations do not form part of the invention but are useful for carrying out the synthesis of the compounds of the invention.

Preparation 1: 3-METHYLBENZOTHIAZOLINONE 1 mol of sodium hydroxide is dissolved in 2000 cm$^3$ of water, 1 mol of benzothiazolinone is added and 1 mol of methyl sulfate is then added dropwise. The mixture is stirred for 3 hours with magnetic stirring at room temperature. The product is drained, washed with water, dried and recrystallized in 2-propanol.

Molar mass: 165.21 g.mol$^{-1}$ for $C_8H_7NOS$
Melting point: 74° C.
Yield: 76%
Rf: 0.7 Eluent: cyclohexane/toluene/acetone (5:2:3)
Infrared spectrometry
2940–2910 cm.$^{-1}$ vCH
1680 cm$^{-1}$ vCO—S
1580 cm$^{-1}$ vC=C

| Nuclear magnetic resonance spectrometry (80 MHz, DMSO-d$_6$) | | | |
|---|---|---|---|
| δ: 3.45 ppm | singlet | 3H | N—CH$_3$ |
| δ: 7.30 ppm | complex | 4H | aromatic |

Preparation 2: 3-METHYLBENZOXAZOLINONE

With magnetic stirring, 1 mol of sodium hydroxide and 1 mol of benzoxazolinone are dissolved in 2000 cm$^3$ of water and 1 mol of methyl sulfate is then added dropwise. Stirring is continued for 3 hours. The precipitate obtained is filtered off and washed with 1% aqueous sodium hydroxide solution (2 times 200 cm$^3$) and then with water until the washing liquors are neutral. The product is dried and recrystallized in 95° strength alcohol.

Molar mass: 149.15 g.mol$^{-1}$ for $C_8H_7NO_2$
Melting point: 86° C.
Yield: 76%
Rf: 0.9 Eluent: methanol (saturated with ammonia)/chloroform (1:9)
Infrared spectrometry
3050 cm$^{-1}$ vCH
1760 cm$^{-1}$ vCO–O
1590 cm$^{-1}$ vC=C

| Nuclear magnetic resonance spectrometry (80 MHz, DMSO-d$_6$) | | | |
|---|---|---|---|
| δ: 3.35 ppm | singlet | 3H | N—CH$_3$ |
| δ: 7.40 ppm | complex | 4H | aromatic |

Preparation 3: 3-METHYL-6-FORMYLBENZOTHIAZOLINONE 0.010 mol of 3-methylbenzothiazolinone and 0.015 mol of hexamethylene tetramine are crushed in a mortar, and the two products are then introduced successively into a round-bottomed flask containing 50 g of polyphosphoric acid at 130° C., with mechanical stirring in an oil bath. The reaction mixture is heated to 130° C. for 20 minutes. After cooling, it is poured into 300 cm$^3$ of ice-cold water. The mixture is stirred for 1 hour. The precipitate is drained, washed with water and dried. The filtrate is extracted 3 times with 30 cm$^3$ of chloroform. The chloroform phases are washed with water, dried over calcium chloride and evaporated under reduced pressure. The product is dried and recrystallized in absolute ethanol.

Molar mass: 193.22 g.mol$^{-1}$ for $C_9H_7NO_2S$
Melting point: 135° C.
Yield: 73%
Rf: 0.8 Eluent: cyclohexane/toluene/acetone (5:2:3)
Infrared spectrometry
1680 cm$^{-1}$ vCO–S and vCO
1590 cm$^{-1}$ vC=C

| Nuclear magnetic resonance spectrometry (80 MHz, DMSO-d$_6$) | | | | |
|---|---|---|---|---|
| δ: 3.45 ppm | singlet | 3H | N—CH$_3$ | |
| δ: 7.50 ppm | doublet | 1H | H$_4$ | $J_{4-5}$ = 8.30 Hz |
| δ: 7.80 ppm | doublet of doublets | 1H | H$_5$ | $J_{5-4}$ = 8.30 Hz |
| | | | | $J_{5-7}$ = 1.30 Hz |
| δ: 8.20 ppm | doublet | 1H | H$_7$ | $J_{7-5}$ = 1.30 Hz |
| δ: 9.90 ppm | singlet | 1H | CHO | |

Note: This compound (Preparation 3) forms part of the invention in the same way as the compounds of formula (I).

Preparation 4: 3-METHYL-6-FORMYLBENZOXAZOLINONE 0.10 mol of 3-methylbenzoxazolinone and 0.15 mol of hexamethylenetetramine are mixed in a mortar. The mixture is introduced into a round-bottomed flask containing 200 g of polyphosphoric acid at 90° C., with stirring in an oil bath. The reaction mixture is heated to 150° C. for 10 minutes while stirring. After cooling, it is poured into 500 cm$^3$ of ice-cold water and stirred for one hour. The precipitate obtained is drained, washed with water and dried. The filtrate is subjected to several extractions with chloroform. The combined chloroform phases are washed with water, dried over calcium chloride and evaporated under reduced pressure. The product obtained, combined with the above precipitate, is recrystallized in water.

Molar mass: 177.16 g.mol$^{-1}$ for $C_9H_7NO3$
Melting point: 146° C.
Yield: 74%
Rf: 0.8 Eluent: methanol (saturated with ammonia)/chloroform (1:9)
Infrared spectrometry
3040 cm$^{-1}$ vCH
1765 cm$^{-1}$ vCO-O 1675 cm$^{-1}$ νCO
1600 cm$^{-1}$ νC=C Nuclear magnetic resonance spectrometry (300 MHz, DMSO-d$_6$)

| δ: 3.40 ppm | singlet | 3H | N—CH$_3$ | |
|---|---|---|---|---|
| δ: 7.50 ppm | doublet | 1H | H$_4$ | J$_{4-5}$ = 8.30 Hz |
| δ: 7.80 ppm | doublet of doublets | 1H | H$_5$ | J$_{5-4}$ = 8.30 Hz |
| | | | | J$_{5-7}$ = 1.30 Hz |
| δ: 8.00 ppm | doublet | 1H | H$_7$ | J$_{7-5}$ = 1.30 Hz |
| δ: 9.80 ppm | singlet | 1H | CHO | |

Preparation 5: 3-METHYL-6-(HYDROXYMETHYL) BENZOTHIAZOLINONE 0.010 mol of 3-methyl-6-formylbenzothiazolinone is introduced at room temperature into 50 cm$^3$ of methanol. 0.015 mol of sodium borohydride is added in small portions with magnetic stirring. After 2 hours of stirring at room temperature, the methanol is evaporated off under reduced pressure and the residue is then taken up with 50 cm$^3$ of water. The precipitate is drained, dried and then recrystallized in 2-propanol.

Molar mass: 195.24 g.mol$^{-1}$ for C$_9$H$_9$NO$_2$S
Melting point: 120° C.
Yield: 79%
Rf: 0.5 Eluent: cyclohexane/toluene/acetone (5:2:3)
Infrared spectrometry
3350 cm$^{-1}$ νOH
2960–2800 cm$^{-1}$ νCH
1670 cm$^{-1}$ νCO—S
1600 cm$^{-1}$ νC=C Nuclear magnetic resonance spectrometry (80 MHz, DMSO-d$_6$)

| δ: 3.40 ppm | singlet | 3H | N—CH$_3$ | |
|---|---|---|---|---|
| δ: 4.50 ppm | singlet | 2H | CH$_2$ | |
| δ: 5.25 ppm | signal | 1H | OH | exchangeable with D$_2$O |
| δ: 7.30 ppm | complex | 2H | H$_4$, H$_5$ | |
| δ: 7.60 ppm | singlet | 1H | H$_7$ | |

Note: This compound (Preparation 5) forms part of the invention in the same way as the compounds of formula (I).

Preparation 6: 3-METHYL-6-HYDROXYMETHYLBENZOXAZOLINONE 0.10 mol of 3-methyl-6-formylbenzoxazolinone is introduced into 150 cm$^3$ of methanol. 0.15 mol of sodium borohydride is added in small portions at room temperature with magnetic stirring. After 2 hours, the methanol is evaporated off under reduced pressure and the residue is taken up with water. The precipitate is drained and then recrystallized in water.

Molar mass: 179.17 g.mol$^{-1}$ for C$_9$H$_9$NO$_3$
Melting point: 127° C.
Yield: 73%
Rf: 0.5 Eluent: methanol (saturated with ammonia)/chloroform (1:9)
Infrared spectrometry
3500–3200 cm$^{-1}$ νOH
3080–2880 cm$^{-1}$ νCH
1755 cm$^{-1}$ μCO—O
1620 cm$^{-1}$ μC=C Nuclear magnetic resonance spectrometry (80 MHz, DMSO-d$_6$)

| δ: 3.35 ppm | singlet | 3H | N—CH$_3$ |
|---|---|---|---|
| δ: 4.55 ppm | singlet | 2H | CH$_2$ |
| δ: 5.25 ppm | signal | 1H | OH | exchangeable with D$_2$O |
| δ: 7.20 ppm | complex | 2H | H$_4$, H$_5$ |
| δ: 7.25 ppm | singlet | 1H | H$_7$ |

Note: This compound (Preparation 6) forms part of the invention in the same way as the compounds of formula (I).

Preparaion 7: 6-HYDROXYMETHYLBENZOXAZOLINONE 0.01 mol of 6-(ethoxycarbonyl)benzoxazolinone and 0.03 mol of lithium aluminum hydride in small portions are introduced into 50 cm$^3$ of tetrahydrofuran cooled in an ice bath. The mixture is stirred at room temperature for one hour. It is hydrolyzed in 100 cm$^3$ of ice-cold water acidified to pH 1 with 6N hydrochloric acid. The product is extacted with three times 50 cm$^3$ of chloroform, and the organic phase is dried and then evaporated. The compound is dried and recrystallized in acetonitrile.

Molar mass: 165.14 g.mol$^{-1}$ for C$_8$H$_7$NO$_3$
Melting point: 153°–154° C.
Yield: 48%
Rf: 0.2 Eluent:methanol (saturated with ammonia)/chloroform (1:9)
Infrared spectrometry
3330 cm$^{-1}$ νOH and νNH
3100–2700 cm$^{-1}$ νCH
1740 cm$^{-1}$ νCO—O
1620 cm$^{-1}$ νC=C Nuclear magnetic resonance spectrometry (80 MHz, DMSO-d$_6$)

| δ: 4.60 ppm | singlet | 2H | CH$_2$ | |
|---|---|---|---|---|
| δ: 5.30 ppm | signal | 1H | OH | exchangeable with D$_2$O |
| δ: 7.00 ppm | complex | 2H | H$_4$, H$_5$ | |
| δ: 7.30 ppm | singlet | 1H | H$_7$ | |
| δ: 11.60 ppm | singlet | 1H | NH | exchangeable with D$_2$O |

Note: This compound (Preparation 7) forms part of the invention in the same way as the compounds of formula (I).

Preparation 8: 3-METHYL-6-(CHLOROMETHYL) BENZOTHIAZOLINONE 0.01 mol of 3-methyl-6-(hydroxymethyl) benzothiazolinone is introduced into 50 cm$^3$ of chloroform. 0.02 mol of thionyl chloride is added dropwise by means of a dropping funnel. The mixture is brought to reflux for 4 hours. The chloroform is evaporated off under reduced pressure, and the residue is then taken up 3 times with absolute ethanol in order to eliminate the traces of thionyl chloride. The product is dried and recrystallized in 2-propanol.

Molar mass: 213.68 g.mol$^{-1}$ for C$_9$H$_8$ClNOS
Melting point: 128° C.
Yield: 95%
Rf: 0.8 Eluent: cyclohexane/toluene/acetone (5:2:3)
Infrared spectrometry
1680 cm$^{-1}$ νCO—S
1600 cm$^{-1}$ νC=C Nuclear magnetic resonance spectrometry (300 MHz, DMSO-d$_6$)

| δ: 3.40 ppm | singlet | 3H | N—CH$_3$ | |
|---|---|---|---|---|
| δ: 4.80 ppm | singlet | 2H | CH$_2$ | |
| δ: 7.25 ppm | doublet | 1H | H$_4$ | J$_{4-5}$ = 8.30 Hz |

-continued

| Nuclear magnetic resonance spectrometry (300 MHz, DMSO-d$_6$) | | | | |
|---|---|---|---|---|
| δ: 7.45 ppm | doublet of doublets | 1H | H$_5$ | J$_{5-4}$ = 8.30 Hz |
| | | | | J$_{5-7}$ = 1.30 Hz |
| δ: 7.75 ppm | doublet | 1H | H$_7$ | J$_{7-5}$ = 1.30 Hz |

Note: This compound (Preparation 8) forms part of the invention in the same way as the compounds of formula (I).

Preparation 9: 3-METHYL-6-(CHLOROMETHYL) BENZOXAZOLINONE 0.10mol of 3-methyl-6-(hydroxymethyl)benzoxazolinone is dissolved in 100 cm$^3$ of chloroform. 0.20 mol of thionyl chloride is added dropwise by means of a dropping funnel. The mixture is brought to reflux for 4 hours. The chloroform is evaporated off under reduced pressure, and the residue is then taken up 3 times with absolute ethanol in order to eliminate the traces of thionyl chloride. The product is dried and then recrystallized in 2-propanol.

Molar mass: 197.62 g.mol$^{-1}$ for C$_9$H$_8$ClNO$_2$
Melting point: 132.5° C.
Yield: 84%
Rf: 0.8 Eluent: methanol (saturated with ammonia)/chloroform (1:9)
Infrared spectrometry
3040 cm$^{-1}$ νCH
1755 cm$^{-1}$ νCO—O
1610 cm$^{-1}$ νC=C

| Nuclear magnetic resonance spectrometry (80 MHz, DMSO-d$_6$) | | | |
|---|---|---|---|
| δ: 3.35 ppm | singlet | 3H | N—CH$_3$ |
| δ: 4.80 ppm | singlet | 2H | CH$_2$ |
| δ: 7.30 ppm | complex | 2H | H$_4$, H$_5$ |
| δ: 7.45 ppm | singlet | 1H | H$_7$ |

Note: This compound (Preparation 9) forms part of the invention in the same way as the compounds of formula (I).

Preparation 10: 6-(CHLOROMETHYL) BENZOXAZOLINONE 0.01 mol of 6-(hydroxymethyl)benzoxazolinone is introduced into 50 cm$^3$ of chloroform. 0.02 mol of thionyl chloride is added dropwise by means of a dropping funnel. The mixture is brought to reflux for 2 hours. The chloroform is evaporated off under reduced pressure, and the residue is then taken up 3 times with absolute ethanol in order to eliminate the traces of thionyl chloride. The product is dried and recrystallized in 2-propanol.

Molar mass: 183.59 g.mol$^{-1}$ for C$_8$H$_6$ClNO$_2$
Melting point: 186–187° C.
Yield: 72%
Rf: 0.5 Eluent: methanol (saturated with ammonia)/chloroform (1:9)
Infrared spectrometry
3200 cm$^{-1}$ νNH
1760 cm$^{-1}$ νCO—O
1610 cm$^{-1}$ νC=C

| Nuclear magnetic resonance spectrometry (80 MHz, DMSO-d$_6$) | | | |
|---|---|---|---|
| δ: 4.80 ppm | singlet | 2H | CH$_2$ |
| δ: 7.20 ppm | complex | 3H | H$_4$, H$_5$, H$_7$ |
| δ: 11.75 ppm | singlet | 1H | NH exchangeable with D$_2$O |

Note: This compound (Preparation 10) forms part of the invention in the same way as the compounds of formula (I).

Preparation 11: 6-HYDROXYMETHYLBENZOTHIAZOLINONE 0.01 mol of 6-(ethoxycarbonyl)benzothiazolinone and 0.03 mol of lithium aluminum hydride in small portions are introduced into 50 cm$^3$ of tetrahydrofuran cooled in an ice bath. The mixture is stirred at room temperature for 30 minutes. It is hydrolyzed in 100 cm$^3$ of ice-cold water acidified to pH 1 with 6N hydrochloric acid. The product is extracted with 3 times 50 cm$^3$ of chloroform, and the organic phase is dried and then evaporated. The compound is dried and recrystallized in acetonitrile.

Molar mass: 181.21 g.mol$^{-1}$ for C$_8$H$_7$NO$_2$S
Melting point: 168–170° C.
Yield: 40 %
Rf: 0.2 Eluent: methanol (saturated with ammonia)/chloroform (1:9)
Infrared spectrometry
3300 cm$^{-1}$ νOH and νNH
3000–2800 cm$^{-1}$ νCH
1650 cm$^{-1}$ νCO—S

| Nuclear magnetic resonance spectrometry (300 MHz, DMSO-d$_6$) | | | | |
|---|---|---|---|---|
| δ: 4.50 ppm | singlet | 2H | CH$_2$ | |
| δ: 5.20 ppm | signal | 1H | OH | exchangeable with D$_2$O |
| δ: 7.10 ppm | doublet | 1H | H$_4$ | J$_{4-5}$ = 8.00 Hz |
| δ: 7.25 ppm | doublet | 1H | H$_5$ | J$_{5-4}$ = 8.00 Hz |
| δ: 7.50 ppm | singlet | 1H | H$_7$ | |
| δ: 11.85 ppm | singlet | 1H | NH | exchangeable with D$_2$O |

Note: This compound (Preparation 11) forms part of the invention in the same way as the compounds of formula (I).

Preparation 12: 6-(CHLOROMETHYL) BENZOTHIAZOLINONE 0.01 mol of 6-(hydroxymethyl)benzothiazolinone is introduced into 50 cm$^3$ of chloroform, and 0.02 mol of thionyl chloride is added dropwise by means of a dropping funnel. The mixture is brought to reflux for 2 hours. The chloroform is evaporated off under reduced pressure, and the residue is then taken up 3 times with absolute ethanol in order to eliminate the traces of thionyl chloride. The product is dried and recrystallized in toluene.

Molar mass: 199.66 g.mol$^{-1}$ for C$_8$H$_6$ClNOS
Melting point: 183–184° C.
Yield: 73%
Rf: 0.6 Eluent: methanol (saturated with ammonia)/chloroform (1:9)
Infrared spectrometry
3140 cm$^{-1}$ νNH
3080–2820 cm$^{-1}$ νCH
1660 cm$^{-1}$ νCO—S
1600 cm$^{-1}$ νC=C

| Nuclear magnetic resonance spectrometry (300 MHz, DMSO-d$_6$) | | | | |
|---|---|---|---|---|
| δ: 4.80 ppm | singlet | 2H | CH$_2$ | |
| δ: 7.10 ppm | doublet | 1H | H$_4$ | J$_{4-5}$ = 8.25 Hz |
| δ: 7.50 ppm | doublet | 1H | H$_5$ | J$_{5-4}$ = 8.25 Hz |
| δ: 7.65 ppm | singlet | 1H | H$_7$ | |
| δ: 12.00 ppm | singlet | 1H | NH | exchangeable with D$_2$O |

Note: This compound (Preparation 12) forms part of the invention in the same way as the compounds of formula (I).

EXAMPLE 1

3-METHYL-6-[(4-(2-METHOXYPHENYL)-1-PIPERAZINYL)METHYL]-BENZOTHIAZOLINONE HYDROCHLORIDE 0.01 mol of 3-methyl-6-(chloromethyl) benzothiazolinone, 0.012 mol of N-(orthomethoxyphenyl)

piperazine hydrochloride and 0.022 mol of triethylamine are added to 20 cm³ of dioxane. The mixture is heated to reflux with magnetic stirring for 6 days. The inorganic residue is filtered off and the dioxane is then evaporated off under reduced pressure. The residue is taken up with 50 cm³ of water, then filtered off and dried. The product is dissolved in the minimum of absolute ethanol, and 100 cm³ of absolute ethanol saturated with gaseous hydrochloric acid are added. The precipitate is filtered off, washed with absolute ethanol, dried and then recrystallized in methanol.

Molar mass: 405.95 g.mol$^{-1}$ for $C_{20}H_{24}ClN_3O_2S$

Melting point: 168° C.

Yield: 33%

Rf: 0.8 Eluent: cyclohexane/toluene/acetone (5:2:3)

Infrared spectrometry

3060–2840 cm$^{-1}$ νCH

2640–2060 cm$^{-1}$ νNH$^+$ 1670 cm$^{-1}$ νCO—S 1600 cm$^{-1}$ νC=C

| Nuclear magnetic resonance spectrometry (300 MHz, DMSO-d$_6$) | | | | |
|---|---|---|---|---|
| δ: 3.00 ppm | complex | 4H | piperazine | |
| δ: 3.40 ppm | complex | 4H | piperazine | |
| δ: 3.45 ppm | singlet | 3H | N—CH$_3$ | |
| δ: 3.80 ppm | singlet | 3H | O—CH$_3$ | |
| δ: 4.40 ppm | singlet | 2H | CH$_2$ | |
| δ: 7.00 ppm | complex | 4H | phenyl | |
| δ: 7.45 ppm | doublet | 1H | H$_4$ | $J_{4-5}$ = 8.30 Hz |
| δ: 7.65 ppm | doublet | 1H | H$_5$ | $J_{5-4}$ = 8.30 Hz |
| δ: 7.90 ppm | singlet | 1H | H$_7$ | |
| δ: 11.00 ppm | signal | 1H | NH$^+$ | exchangeable with D$_2$O |

EXAMPLE 2

3-METHYL-6-[(4-(2-METHOXYPHENYL)-1-PIPERAZINYL)-METHYL] BENZOXAZOLINONE HYDROCHLORIDE 0.010 mol of 3-methyl-6-(chloromethyl) benzoxazolinone, 0.020 mol of triethylamine, 0.012 mol of N-(ortho-methoxyphenyl)piperazine and 0.001 mol of potassium iodide are added to 50 cm³ of acetone. The mixture is heated to reflux with magnetic stirring for 4 days. The inorganic residue is filtered off and the filtrate is then evaporated to dryness under reduced pressure. 20 cm³ of 1N hydrochloric acid and 30 cm³ of ethyl acetate are added. The mixture is left stirring for 30 minutes. The precipitate is filtered off, washed several times with ethyl acetate, dried and then recrystallized in methanol.

Molar mass: 389.88 g.mol$^{-1}$ for $C_{20}H_{24}ClN_3O_3$

Melting point: >260° C. (hydrochloride form)

Melting point:: 149–150° C. (base form)

Yield: 52%

Rf: 0.8 Eluent: methanol (saturated with ammonium)/chloroform (1:9)

Infrared spectrometry

3060–2820 cm$^{-1}$ νCH

2700–2300 cm$^{-1}$ νNH+

1780 cm$^{-1}$ νCO—O 1610 cm$^{-1}$ νC=C 1590 cm$^{-1}$ νC=C

| Nuclear magnetic resonance spectrometry (300 MHz, DMSO-d$_6$) | | | | |
|---|---|---|---|---|
| δ: 3.05 ppm | complex | 4H | piperazine | |
| δ: 3.40 ppm | complex | 7H | N—CH$_3$, piperazine | |
| δ: 3.80 ppm | singlet | 3H | O—CH$_3$ | |
| δ: 4.40 ppm | singlet | 2H | CH$_2$ | |
| δ: 6.95 ppm | complex | 4H | phenyl | |
| δ: 7.40 ppm | doublet | 1H | H$_4$ | $J_{4-5}$ = 8.00 Hz |
| δ: 7.50 ppm | doublet | 1H | H$_5$ | $J_{5-4}$ = 8.00 Hz |
| δ: 7.65 ppm | singlet | 1H | H$_7$ | |
| δ: 11.45 ppm | signal | 1H | NH$^+$ | exchangeable with D$_2$O |

EXAMPLE 3

3-METHYL-6-[(4-(2-FLUOROPHENYL)-1-PIPERAZINYL)METHYL]-BENZOTHIAZOLINONE 0.01 mol of 3-methyl-6-(chloromethyl) benzothiazolinone, 0.01 fluoroph-(orthofluorophenyl) piperazine and 0.01 mol of triethylamine are added to 20 cm³ of dioxane. The mixture is heated to reflux with magnetic stirring for 3 days. The inorganic residue is filtered off and the dioxane is then evaporated off under reduced pressure. The residue is taken up with 50 cm³ of water, then filtered off, dried and recrystallized in 1-propanol.

Molar mass: 357.45 g.mol$^{-1}$ for $C_{19}H_{20}FN_3OS$

Melting point: 152° C.

Yield: 60%

Rf: 0.8 Eluent: cyclohexane/toluene/acetone (5:2:3)

Infrared spectrometry

2960–2760 cm$^{-1}$ νCH 1670 cm$^{-1}$ νCO—S 1600 cm$^{-1}$ νC=C

| Nuclear magnetic resonance spectrometry (300 MHz, DMSO-d$_6$) | | | | |
|---|---|---|---|---|
| δ:3.00 ppm | complex | 4H | piperazine | |
| δ:3.35 ppm | complex | 4H | piperazine | |
| δ:3.40 ppm | singlet | 3H | N—CH$_3$ | |
| δ:3.55 ppm | singlet | 2H | CH$_2$ | |
| δ:7.00 ppm | complex | 4H | phenyl | |
| δ:7.25 ppm | doublet | 1H | H$_4$ | $J_{4-5}$ = 8.25 Hz |
| δ:7.35 ppm | doublet | 1H | H$_5$ | $J_{5-4}$ = 8.25 Hz |
| δ:7.65 ppm | singlet | 1H | H$_7$ | |

EXAMPLE 4

3-METHYL-6-[(4-(2-FLUOROPHENYL)-1-PIPERAZINYL)METHYL] BENZOXAZOLINONE HYDROCHLORIDE

The procedure is identical to that described for obtaining Example 2, replacing N-(ortho-methoxyphenyl)piperazine by N-(ortho-fluorophenyl)piperazine.

Reaction time: 3 days

Molar mass: 377.84 g.mol$^{-1}$ for $C_{19}H_{21}ClFN_3O_2$

Melting point: >260° C. (hydrochloride form)

Melting point: 134–135° C. (base form)

Yield: 50%

Recrystallization solvent: methanol

Rf: 0.8 Eluent: methanol (saturated with ammonia)/chloroform (1:9)

Infrared spectrometry
3040–2820 cm$^{-1}$ νCH
2740–2320 cm$^{-1}$ νNH$^+$
1770 cm$^{-1}$ νCO—O
1610 cm$^{-1}$ νC=C

| Nuclear magnetic resonance spectrometry (300 MHz, DMSO-d$_6$) | | | |
|---|---|---|---|
| δ: 3.15 ppm | complex | 4H | piperazine |
| δ: 3.20 ppm | singlet | 3H | N—CH$_3$ |
| δ: 3.50 ppm | complex | 4H | piperazine |
| δ: 4.40 ppm | singlet | 2H | CH$_2$ |
| δ: 7.10 ppm | complex | 4H | phenyl |
| δ: 7.40 ppm | multiplet | 1H | H$_4$ |
| δ: 7.45 ppm | multiplet | 1H | H$_5$ |
| δ: 7.65 ppm | singlet | 1H | H$_7$ |
| δ: 11.05 ppm | signal | 1H | NH$^+$ exchangeable with D$_2$O |

EXAMPLE 5

3-METHYL-6-[(4-(4-CHLOROPHENYL)-1-PIPERAZINYL)METHYL]-BENZOTHIAZOLINONE

The procedure is identical to that described for obtaining Example 2, replacing N-(ortho-methoxyphenyl)piperazine by N-(para-chlorophenyl)piperazine and 3-methyl-6-(chloromethyl)benzoxazolinone by 3-methyl-6-(chloromethyl)benzothiazolinone. The product in hydrochloride form is obtained in base form in ethyl acetate in the presence of triethylamine.

Reaction time: 2 days
Molar mass: 373.90 g.mol$^{-1}$ for C$_{19}$H$_{20}$ClN$_3$OS
Melting point: 162–163° C.
Yield: 45%
Recrystallization solvent: methanol
Rf: 0.7 Eluent: methanol (saturated with ammonia/chloroform (1:9)
Infrared spectrometry
2960–2740 cm$^{-1}$ νCH
1660 cm$^{-1}$ νCO—S
1590 cm$^{-1}$ νC=C

| Nuclear magnetic resonance spectrometry (300 MHz, DMSO-d$_6$) | | | |
|---|---|---|---|
| δ: 2.50 ppm | complex | 4H | piperazine |
| δ: 3.10 ppm | complex | 4H | piperazine |
| δ: 3.40 ppm | singlet | 3H | N—CH$_3$ |
| δ: 3.55 ppm | singlet | 2H | CH$_2$ |
| δ: 6.90 ppm | complex | 2H | H$_4$, H$_5$ |
| δ: 7.30 ppm | complex | 4H | phenyl |
| δ: 7.60 ppm | singlet | 1H | H$_7$ |

EXAMPLE 6

3-METHYL-6-[(4-(4-CHLOROPHENYL)-1-PIPERAZINYL)METHYL]-BENZOXAZOLINONE

The procedure is identical to that described for obtaining Example 2, replacing N-(ortho-methoxyphenyl)piperazine by N-(para-chlorophenyl)piperazine. The product in hydrochloride form is converted to base form in ethyl acetate in the presence of triethylamine.

Reaction time: 3 days
Molar mass: 357.84 g.mol$^{-1}$ for C$_{19}$H$_{20}$ClN$_3$O$_2$
Melting point: 165–166° C.
Yield: 65%
Recrystallization solvent: methanol
Rf: 0.8 Eluent: methanol (saturated with ammonia)/chloroform (1:9)
Infrared spectrometry
2960–2740 cm$^{-1}$ νCH
1760 cm$^{-1}$ νCO—O
1615cm$^{-1}$ νC=C
1590 cm$^{-1}$ νC=C

| Nuclear magnetic resonance spectrometry (300 MHz, DMSO-d$_6$) | | | |
|---|---|---|---|
| δ: 2.50 ppm | complex | 4H | piperazine |
| δ: 3.10 ppm | complex | 4H | piperazine |
| δ: 3.35 ppm | singlet | 3H | N—CH$_3$ |
| δ: 3.55 ppm | singlet | 2H | CH$_2$ |
| δ: 6.90 ppm | complex | 2H | H$_4$, H$_5$ |
| δ: 7.20 ppm | complex | 4H | phenyl |
| δ: 7.30 ppm | singlet | 1H | H$_7$ |

EXAMPLE 7

4-METHYL-7-[(4-(2-METHOXYPHENYL)-1-PIPERAZINYL)METHYL]-3-OXO-3,4-DIHYDRO-2H-1,4BENZOXAZINE

Stage A: 5-[(4-(2-METHOXYPHENYL)-1-PIPERAZINYL)METHYL]-2-(METHYLAMINO)PHENOL

Note: This compound forms part of the invention in the same way as Example 7.

0.08 mol of sodium hydroxide is dissolved in 5 cm$^3$ of water, and 25 cm$^3$ of methanol and 0.01 mol of 3-methyl-6-[(4-(ortho-methoxyphenyl)-1-piperazinyl)methyl] benzoxazolinone hydrochloride are then added. The mixture is heated to reflux with magnetic stirring for 2 hours. The methanol is evaporated off under reduced pressure and the residue is then dissolved in 50 cm$^3$ of water. The solution is placed in a bath of ice-cold water, 6N hydrochloric acid is added until the pH=1, and the mixture is then alkalinized with 10% aqueous potassium carbonate solution until the pH=8–9. The mixture is stirred for 30 minutes. The precipitate is filtered off, washed with water until the washing liquors are neutral, dried and then recrystallized in toluene.

Molar mass: 363.88 g.mol$^{-1}$ for C$_{19}$H$_{26}$ClN$_3$O$_2$
Melting point: 155–156° C.
Yield: 67%
Rf: 0.7 Eluent: methanol (saturated with ammonia)/chloroform (1:9)
Infrared spectrometry
3500 cm$^{-1}$ νOH
3180 cm$^{-1}$ νNH
2980–2800 cm$^{-1}$ νCH
2720–2520 cm$^{-1}$ νNH$^+$
1620 cm$^{-1}$ νC=C
1590 cm$^{-1}$ νC=C

| Nuclear magnetic resonance spectrometry (300 MHz, DMSO-d$_6$) | | | |
|---|---|---|---|
| δ: 2.75 ppm | singlet | 3H | N—CH$_3$ |
| δ: 3.10 ppm | complex | 4H | piperazine |

-continued

| Nuclear magnetic resonance spectrometry (300 MHz, DMSO-$d_6$) | | | |
|---|---|---|---|
| δ: 3.40 ppm | singlet | 4H | piperazine |
| δ: 3.80 ppm | singlet | 3H | O—$CH_3$ |
| δ: 4.10 ppm | singlet | 2H | $CH_2$ |
| δ: 5.10 ppm | signal | 1H | OH exchangeable with $D_2O$ |
| δ: 6.40 ppm | doublet | 1H | $H_3 J_{3-4}$ = 7.95 Hz |
| δ: 6.95 ppm | complex | 6H | $H_4$, $H_6$ and phenyl |
| δ: 9.60 ppm | singlet | 1H | NH exchangeable with $D_2O$ |
| δ: 10.80 ppm | signal | 1H | NH* exchangeable with $D_2O$ |

Stage B: 4-METHYL-7-[(4-(2-METHOXYPHENYL)-1-PIPERAZINYL)METHYL]-3-OXO-3,4-DIHYDRO-2H-1,4-BENZOXAZINE 0.01 mol of sodium is dissolved in 40 cm³ of absolute ethanol. The absolute ethanol is evaporated off, and 20 cm³ of dimethyl sulfoxide and 0.01 mol of 5-[(4-(orthomethoxyphenyl)-1-piperazinyl)methyl]-2-(methylamino)phenol are then added. The mixture is stirred for 30 minutes, 0.01 mol of ethyl bromoacetate is added and the mixture is then left for 16 hours at room temperature with magnetic stirring. It is hydrolyzed in 100 cm³ of ice-cold water, and the solution is acidified with 1N hydrochloric acid until the pH=1 and then alkalinized with 10% aqueous potassium carbonate solution until the pH=8–9. The product is extracted 3 times with 30 cm³ of ethyl acetate. The organic phase is washed with water, dried over magnesium sulfate and then evaporated under reduced pressure. The residue is washed with ether, the mixture is then filtered and the ether is evaporated off under reduced pressure. The product is dried and recrystallized in absolute ethanol.

Molar mass: 367.44 g.mol$^{-1}$ for $C_{21}H_{25}N_3O_3$
Melting point: 141–143° C.
Yield: 41%
Rf: 0.8 Eluent: methanol (saturated with ammonia)/chloroform (1:9)
Infrared spectrometry
2980–2740 cm$^{-1}$ νCH
1670 cm$^{-1}$ νCO
1585 cm$^{-1}$ νC=C

| Nuclear magnetic resonance spectrometry (300 MHz, DMSO-$d_6$) | | | |
|---|---|---|---|
| δ: 2.50 ppm | complex | 4H | piperazine |
| δ: 2.95 ppm | complex | 4H | piperazine |
| δ: 3.30 ppm | singlet | 3H | N—$CH_3$ |
| δ: 3.45 ppm | singlet | 2H | $CH_2$ |
| δ: 3.75 ppm | singlet | 3H | O—$CH_3$ |
| δ: 4.65 ppm | singlet | 4H | $H_2$ (benzoxazine) |
| δ: 7.00 ppm | complex | 7H | $H_5$, $H_6$, $H_8$ and phenyl |

EXAMPLE 8

4-METHYL-7-[(4-(2-FLUOROPHENYL)-1-PIPERAZINYL)METHYL]-3-OXO-3,4-DIHYDRO-2H-1,4-BENZOXAZINE

Stage A: 5-[(4-(2-FLUOROPHENYL)-1 -PIPERAZINYL)METHYL]-2-(METHYLAMINO)PHENOL

Note: This compound forms part of the invention in the same way as the compound of Example 8.

The procedure is identical to that described for Example 7 Stage A, replacing 3-methyl-6-[(4-(ortho-methoxyphenyl)-1-piperazinyl)methyl]benzoxazolinone hydrochloride by 3-methyl-6-[(4-(ortho-fluorophenyl)-1-piperazinyl)methyl]benzoxazolinone hydrochloride.

Reaction time: 2 hours
Molar mass: 315.39 g.mol$^{-1}$ for $C_{18}H_{22}FN_3O$
Melting point: 170–171 ° C.
Yield: 79%
Recrystallization solvent: toluene
Rf: 0.5 Eluent: methanol (saturated with ammonia)/chloroform (1:9)
Infrared spectrometry
3420 cm$^{-1}$ νOH and νNH
3040–2780 cm$^1$ νCH
1610 cm$^{-1}$ νC=C

| Nuclear magnetic resonance spectrometry (300 MHz, DMSO-$d_6$) | | | |
|---|---|---|---|
| δ: 2.50 ppm | complex | 4H | piperazine |
| δ: 2.70 ppm | singlet | 3H | N—$CH_3$ |
| δ: 3.00 ppm | complex | 4H | piperazine |
| δ: 3.35 ppm | multiplet | 2H | $CH_2$ |
| δ: 4.70 ppm | signal | 1H | OH exchangeable with $D_2O$ |
| δ: 6.35 ppm | doublet | 1H | $H_3 J_{3-4}$ = 8.15 Hz |
| δ: 6.50 ppm | doublet | 1H | $H_4 J_{4-3}$ = 8.15 Hz |
| δ: 6.60 ppm | singlet | 1H | $H_6$ |
| δ: 7.00 ppm | complex | 4H | phenyl |
| δ: 9.20 ppm | singlet | 1H | NH exchangeable with $D_2O$ |

Stage B: 4-METHYL-7-[(4-(2-FLUOROPHENYL)-1-PIPERAZINYL)METHYL]-3-OXO-3,4-DIHYDRO-2H-1,4-BENZOXAZINE The procedure is identical to that described for obtaining Example 7 Stage B from Example 7 Stage A, using the compound obtained in Example 8 Stage A.

Reaction time: 16 hours
Molar mass: 355.41 g.mol$^{-1}$ for $C_{20}H_{22}FN_3O_2$
Melting point: 126–128° C.
Yield: 36%
Recrystallization solvent: absolute ethanol
Rf: 0.8 Eluent: methanol (saturated with ammonia)/chloroform (1:9)
Infrared spectrometry
3000–2740 cm$^{-1}$ νCH
1670 cm$^1$ νCO
1605 cm$^{-1}$ νC=C

| Nuclear magnetic resonance spectrometry (300 MHz, DMSO-$d_6$) | | | |
|---|---|---|---|
| δ: 2.50 ppm | complex | 4H | piperazine |
| δ: 3.00 ppm | complex | 4H | piperazine |
| δ: 3.30 ppm | singlet | 3H | N—$CH_3$ |
| δ: 3.50 ppm | singlet | 2H | $CH_2$ |
| δ: 4.65 ppm | singlet | 2H | $H_2$ (benzoxazine) |
| δ: 7.00 ppm | complex | 7H | $H_5$, $H_6$, $H_8$, phenyl |

EXAMPLE 9

4-METHYL-7-[(4-(4-CHLOROPHENYL)-1-PIPERAZINYL)METHYL]-3-OXO-3,4-DIHYDRO-2H-1,4-BENZOXAZINE

Stage A: 5-[(4-(4-CHLOROPHENYL)-1-PIPERAZINYL)METHYL]-2-(METHYLAMINO)]PHENOL

This product forms part of the invention in the same way as Example 9, for which it constitutes a synthesis intermediate.

The procedure is identical to that described for obtaining Example 8 Stage A, using as starting material 3-methyl-6-[(4-(4-para-chlorophenyl)-1 -piperazinyl)methyl)]benzoxazolinone.

Reaction time: 2 hours
Molar mass: 331.84 g.mol$^{-1}$ for $C_{18}H_{22}ClN_3O$
Melting point: 159–160° C.

Yield: 76%
Recrystallization solvent: toluene
Rf: 0.4 Eluent: methanol (saturated with ammonia)/chloroform (1:9)
Infrared spectrometry
3380 cm$^{-1}$ vOH and vNH
2940–2780 cm$^{-1}$ vCH
1610 cm$^{-1}$ vC=C
1590 cm$^{-1}$ vC=C

| Nuclear magnetic resonance spectrometry (300 MHz, DMSO-d$_6$) | | | |
|---|---|---|---|
| δ: 2.30 ppm | complex | 4H | piperazine |
| δ: 2.70 ppm | singlet | 3H | N—CH$_3$ |
| δ: 3.10 ppm | complex | 4H | piperazine |
| δ: 3.35 ppm | singlet | 2H | CH$_2$ |
| δ: 4.70 ppm | signal | 1H | OH exchangeable with D$_2$O |
| δ: 6.35 ppm | doublet | 1H | H$_3$ J$_{3-4}$ = 7.90 Hz |
| δ: 6.50 ppm | doublet | 1H | H$_4$ J$_{4-3}$ = 7.90 Hz |
| δ: 6.60 ppm | singlet | 1H | H$_6$ |
| δ: 6.90 ppm | doublet | 2H | H$_{1'}$, H$_{5'}$ (phenyl) J$_{1'-2'}$ = J$_{5'-4'}$ = 8.65 Hz |
| δ: 7.20 ppm | doublet | 2H | H$_{2'}$, H$_{4'}$ (phenyl) J$_{2'-1'}$ = J$_{4'-5'}$ = 8.65 Hz |
| δ: 9.20 ppm | singlet | 1H | NH exchangeable with D$_2$O |

Stage B: 4-METHYL-7-[(4-(4-CHLOROPHENYL)-1-PIPERAZINYL)METHYL]-3-OXO-3,4-DIHYDRO-2H-1,4-BENZOXAZINE HYDROCHLORIDE The procedure is identical to that described for obtaining Example 7 Stage B, using as starting material the product obtained in Stage A of Example 9. The product is purified on a column of silica gel with the eluent: dichloromethane/methanol (9.9:0.1). The compound is solubilized in the minimum of acetone, and 100 cm$^3$ of anhydrous ether saturated with gaseous hydrochloric acid are added. The precipitate is filtered off, washed with ether, dried and then recrystallized.

Molar mass: 408.32 g.mol$^{-1}$ for C$_{20}$H$_{23}$Cl$_2$N$_3$O$_2$
Melting point: 243–244° C.
Yield: 32%
Recrystallization solvent: 95° strength ethanol
Rf: 0.8 Eluent: methanol (saturated with ammonia)/chloroform (1:9)
Infrared spectrometry
2980–2820 cm$^{-1}$ vCH
2720–2300 cm$^{-1}$ vNH$^+$
1685 cm$^{-1}$ vCO
1615 cm$^{-1}$ vC=C
1590 cm$^{-1}$ vC=C

| Nuclear magnetic resonance spectrometry (300 MHz, DMSO-d$_6$) | | | |
|---|---|---|---|
| δ: 3.30 ppm | complex | 11H | N—CH$_3$, and piperazine |
| δ: 4.30 ppm | singlet | 2H | CH$_2$ |
| δ: 4.70 ppm | singlet | 2H | H$_2$ (benzoxazine) |
| δ: 7.00 ppm | complex | 2H | H$_5$, H$_6$ |
| δ: 7.30 ppm | complex | 5H | H$_8$ and phenyl |
| δ: 11.60 ppm | signal | 1H | NH$^+$ exchangeable with D$_2$O |

EXAMPLE 10

6-[(4-(2-FLUOROPHENYL)-1-PIPERAZINYL)METHYL]-BENZOXAZOLINONE 0.010 mol of 6-(chloromethyl)benzoxazolinone, 0.012 mol of N-(ortho)-fluorophenylpiperazine, 0.020 mol of triethylamine and 0.001 mol of potassium iodide are added to 50 cm$^3$ of acetone. The mixture is heated to reflux for 2 days with magnetic stirring. The inorganic residue is filtered off and the acetone is evaporated off. 30 cm$^3$ of 1N hydrochloric acid and 20 cm$^3$ of ethyl acetate are added. The mixture is left for 30 minutes with magnetic stirring. The precipitate obtained is filtered off and washed several times with ethyl acetate. The product in hydrochloride form is obtained in base form in ethyl acetate in the presence of triethylamine. The product is dried and then recrystallized in toluene.

Molar mass: 327.36 g.mol$^{-1}$ for C$_{18}$H$_{18}$FN$_3$O$_2$
Melting point: 177–179° C.
Yield: 46%
Rf: 0.4 Eluent: methanol (saturated with ammonia)/chloroform (1:9)
Infrared spectrometry
3240 cm$^{-1}$ vNH
2960–2740 cm$^{-1}$ vCH
1760 cm$^{-1}$ vCO—O
1610 cm$^{-1}$ vC=C

| Nuclear magnetic resonance spectrometry (300 MHz, DMSO-d$_6$) | | | |
|---|---|---|---|
| δ: 2.50 ppm | complex | 4H | piperazine |
| δ: 3.00 ppm | complex | 4H | piperazine |
| δ: 3.50 ppm | singlet | 2H | CH$_2$ |
| δ: 7.00 ppm | complex | 6H | H$_4$, H$_5$ and phenyl |
| δ: 7.20 ppm | singlet | 1H | H$_7$ |
| δ: 11.50 ppm | singlet | 1H | NH exchangeable with D$_2$O |

EXAMPLE 11

3-[2-(4-(4-FLUOROBENZOYL)-1-PIPERIDYL)ETHYL]-6-[(4-(2-FLUOROPHENYL)-1-PIPERAZINYL)METHYL]BENZOXAZOLINONE 0.010 mol of 6-[(4-(ortho-fluorophenyl)-1-piperazinyl)methyl]benzoxazolinone and 0.060 mol of potassium carbonate are introduced into 50 cm$^3$ of anhydrous dimethylformamide. The mixture is stirred for 30 minutes under reflux and 0.012 mol of 1-(2-chloroethyl)-4-(para-fluorobenzoyl)piperidine hydrochloride is added. The mixture is heated to reflux for 3 hours with magnetic stirring. It is cooled, the inorganic solid is filtered off and the filtrate is poured into 100 cm$^3$ of ice-cold water. The precipitate formed is filtered off, washed with water, dried and then recrystallized in absolute ethanol.

Molar mass: 560.64 g.mol$^{-1}$ for C$_{32}$H$_{34}$F$_2$N$_4$O$_3$
Melting point: 124–126° C.
Yield: 82%
Rf: 0.7 Eluent: methanol (saturated with ammonia)/chloroform (1:9)
Infrared spectrometry
2960–2740 cm$^{-1}$ vCH
1775 cm$^{-1}$ vCO—O
1670 cm$^{-1}$ vCO
1600 cm$^{-1}$ vC=C

| Nuclear magnetic resonance spectrometry (300 MHz, DMSO-d$_6$) | | | |
|---|---|---|---|
| δ: 1.45 ppm | multiplet | 2H | piperidine |
| δ: 1.70 ppm | multiplet | 2H | piperidine |
| δ: 2.15 ppm | multiplet | 2H | piperidine |
| δ: 2.50 ppm | complex | 4H | piperazine |
| δ: 2.65 ppm | triplet | 2H | CH$_2$-piperidine J$_{e-d}$ = 5.95 Hz |
| δ: 3.00 ppm | complex | 6H | piperazine and piperdine |

-continued

| Nuclear magnetic resonance spectrometry (300 MHz, DMSO-$d_6$) | | | |
|---|---|---|---|
| δ: 3.35 ppm | multiplet | 1H | piperidine-CO |
| δ: 3.55 ppm | singlet | 2H | CH$_2$-piperazine |
| δ: 3.90 ppm | triplet | 2H | CH$_2$—CH$_2$-piperidine $J_{d-e}$ = 5.95 Hz |
| δ: 7.05 ppm | complex | 5H | H$_4$ and phenyl(piperazine) |
| δ: 7.30 ppm | complex | 4H | H$_5$, H$_7$ and benzoyl(piperidine) |
| δ: 8.00 ppm | complex | 2H | benzoyl(piperidine) |

EXAMPLE 12

6-[(4-(2-FLUOROPHENYL)-1-PIPERAZINYL) METHYL]-BENZOTHIAZOLINONE HYDROCHLORIDE 0.010 mol of 6-(chloromethyl)benzothiazolinone, 0.012 mol of N-(ortho-fluorophenyl)-piperazine, 0.020 mol of triethylamine and 0.001 mol of potassium iodide are added to 50 cm$^3$ of acetone. The mixture is heated to reflux for 2 days with magnetic stirring. The inorganic residue is filtered off and the acetone is evaporated off. 30 cm$^3$ of 1N hydrochloric acid and 20 cm$^3$ of ethyl acetate are added. The mixture is left for 30 minutes with magnetic stirring. The precipitate obtained is filtered off and washed several times with ethyl acetate. The product is dried and then recrystallized in 95° strength ethanol.

Molar mass: 379.88 g.mol$^{-1}$ for $C_{18}H_{19}ClFN_3OS$

Melting point: >260° C.

Yield: 61%

Rf: 0.5 Eluent: methanol (saturated with ammonia)/ chloroform (1:9)

Infrared spectrometry 3120 cm$^{-1}$ νNH

2940–2820 cm$^{-1}$ νCH

2740–2540 cm$^{-1}$ νNH$^+$ 1670 cm$^1$ νCO—S 1610 cm$^{-1}$ νC═C

| Nuclear magnetic resonance spectrometry (300 MHz, DMSO-$d_6$) | | | |
|---|---|---|---|
| δ: 3.10 ppm | complex | 4H | piperazine |
| δ: 3.50 ppm | complex | 4H | piperazine |
| δ: 4.50 ppm | singlet | 2H | CH$_2$ |
| δ: 7.10 ppm | complex | 5H | H$_4$ phenyl |
| δ: 7.50 ppm | doublet | 1H | H$_5$ $J_{5-4}$ = 8.20 Hz |
| δ: 7.80 ppm | singlet | 1H | H$_7$ |
| δ: 9.70 ppm | signal | 1H | NH$^+$ exchangeable with D$_2$O |
| δ: 12.15 ppm | singlet | 1H | NH exchangeable with D$_2$O |

EXAMPLE 13

3-[2-(4-(4-FLUOROBENZOYL)-1-PIPERIDYL) ETHYL]-6-[(4-(2-FLUOROPHENYL)-1-PIPERAZINYL)METHYL]-BENZOTHIAZOLINONE DIHYDROCHLORIDE 0.010 mol of 6-[(4-(ortho-fluorophenyl)-1-piperazinyl) methyl]benzothiazolinone and 0.060 mol of potassium carbonate are introduced into 50 cm$^3$ of anhydrous dimethyl formamide. The mixture is stirred for 30 minutes under reflux and 0.012 mol of 1-(2-chloroethyl)-4-(para-fluorobenzoyl)piperidine hydrochloride is added. The mixture is heated to reflux for 1 hour with magnetic stirring. It is cooled, the inorganic solid is filtered off and the filtrate is poured into 100 cm$^3$ Of ice-cold water. The precipitate formed is filtered off, washed with water and then dried. The product is solubilized in the minimum of acetone, and 100 cm$^3$ of anhydrous ether saturated with gaseous hydrochloric acid are added. The precipitate is filtered off, washed with ether, dried and then recrystallized in absolute ethanol.

Molar mass: 649.63 g.mol$^{-1}$ for $C_{32}H_{36}Cl_2F_2N_4O_2S$

Melting point: 251–253° C.

Yield: 56%

Rf: 0.6 Eluent: methanol (saturated with ammonia)/ chloroform (1:9)

Infrared spectrometry

3060–2800 cm$^{-1}$ νCH

2740–2280 cm$^{-1}$ νNH$^+$ 1670 cm$^{-1}$ νCO—S and νCO 1590 cm$^{-1}$ νC═C

| Nuclear magnetic resonance spectrometry (300 MHz, DMSO-$d_6$) | | | |
|---|---|---|---|
| δ: 2.00 ppm | complex | 4H | piperidine |
| δ: 3.20 ppm | complex | 4H | piperazine |
| δ: 3.45 ppm | complex | 11H | piperazine, piperidine, CH$_2$-piperidine |
| δ: 4.45 ppm | complex | 4H | CH$_2$-piperazine, CH$_2$—CH$_2$piperidine |
| δ: 7.10 ppm | complex | 4H | phenyl(piperazine) |
| δ: 7.40 ppm | complex | 2H | H$_4$, H$_5$ |
| δ: 4.45 ppm | complex | 4H | CH$_2$-piperazine |
| δ: 7.80 ppm | complex | 2H | benzoyl(piperidine) |
| δ: 8.00 ppm | singlet | 1H | H$_7$ |
| δ: 8.10 ppm | complex | 2H | benzoyl(piperidine) |
| δ: 11.25 ppm | signal | 1H | NH$^+$ exchangeable with D$_2$O |
| δ: 11.70 ppm | signal | 1H | NH$^+$ exchangeable with D$_2$O |

EXAMPLE 14

3-METHYL-6-[(4-(BENZO[d]-1,2-THIAZOLYL)-1-PIPERAZINYL)METHYL] BENZOTHIAZOLINONE 0.010 mol of 3-methyl-6-(chloromethyl) benzothiazolinone, 0.012 mol of 1-(3-benzisothiazolyl) piperazine, 0.020 mol of triethylamine and 0.001 mol of potassium iodide are added to 50 cm$^3$ of acetone. The mixture is heated to reflux with magnetic stirring for 2 days. The inorganic residue is filtered off and the acetone is evaporated off. 30 cm$^3$ of 1N hydrochloric acid and 20 cm$^3$ of ethyl acetate are added. The mixture is left for 30 minutes with magnetic stirring. The precipitate obtained is filtered off and washed several times with ethyl acetate. The product in hydrochloride form is converted to base form in ethyl acetate in the presence of triethylamine. The product is dried and then recrystallized in methanol.

Molar mass: 396.53 g.mol$^{-1}$ for $C_{20}H_{20}N_4OS_2$

Melting point: 163–165° C.

Yield: 31%

Rf: 0.8 Eluent: methanol (saturated with ammonia)/ chloroform (1:9)

Infrared spectrometry

2980–2760 cm$^{-1}$ νCH 1665 cm$^{-1}$ νCO—S 1580 cm$^{-1}$ νC═C

| Nuclear magnetic resonance spectrometry (300 MHz, DMSO-$d_6$) | | | |
|---|---|---|---|
| δ: 2.60 ppm | complex | 4H | piperazine |
| δ: 3.40 ppm | complex | 7H | N—CH$_3$, and piperazine |
| δ: 3.60 ppm | singlet | 2H | CH$_2$ |
| δ: 7.30 ppm | doublet | 1H | H$_4$ J$_{4-5}$ = 8.00 Hz |
| δ: 7.40 ppm | doublet | 1H | H$_5$ J$_{5-4}$ = 8.00 Hz |
| δ: 7.50 ppm | complex | 2H | benzisothiazole |
| δ: 7.65 ppm | singlet | 1H | H$_7$ |
| δ: 8.05 ppm | complex | 2H | benzisothiazole |

EXAMPLE 15

3-METHYL-6-[(4-(BENZO[d]-1,2-THIAZOLYL)-1-PIPERAZINYL)-METHYL]BENZOXAZOLINONE 0.010 mol of 3-methyl-6-(chloromethyl)benzoxazolinone, 0.012 mol of 1-(3-benzisothiazolyl)piperazine, 0.020 mol of triethylamine and 0.001 mol of potassium iodide are added to 50 cm$^3$ of acetone. The mixture is heated to reflux with magnetic stirring for 3 days. The inorganic residue is filtered off and the acetone is evaporated off. 30 cm$^3$ of 1N hydrochloric acid and 20 cm$^3$ of ethyl acetate are added. The mixture is left for 30 minutes with magnetic stirring. The precipitate obtained is filtered off and washed several times with ethyl acetate. The product in hydrochloride form is converted to base form in ethyl acetate in the presence of triethylamine. The product is dried and then recrystallized in absolute ethanol.

Molar mass: 380.47 g.mol$^{-1}$ for C$_{20}$H$_{20}$N$_4$O$_2$S

Melting point: 193–194° C.

Yield: 72%

Rf: 0.6 Eluent: methanol (saturated with ammonia)/chloroform (1:9)

Infrared spectrometry

3080–2760 cm$^{-1}$ νCH 1760 cm$^{-1}$ νC—O 1620 cm$^{-1}$ νC=C 1590 cm$^{-1}$ νC=C

| Nuclear magnetic resonance spectrometry (300 MHz, DMSO-$d_6$) | | | |
|---|---|---|---|
| δ: 2.60 ppm | complex | 4H | piperazine |
| δ: 3.35 ppm | singlet | 3H | N—CH$_3$ |
| δ: 3.50 ppm | complex | 4H | piperazine |
| δ: 3.60 ppm | singlet | 2H | CH$_2$ |
| δ: 7.20 ppm | complex | 2H | H$_4$, H$_5$ |
| δ: 7.30 ppm | singlet | 1H | H$_7$ |
| δ: 7.50 ppm | complex | 2H | benzisothiazole |
| δ: 8.05 ppm | complex | 2H | benzisothiazole |

EXAMPLE 16

4-METHYL-7-[(4-(BENZO[d]-1,2-THIAZOLYL)-1-PIPERAZINYL)METHYL]-3-OXO-3,4-DIHYDRO-2H-1,4-BENZO-XAZINE HYDROCHLORIDE

Stage A: 5-[(4-(3-BENZISOTHIAZOLYL)-1-PIPERAZINYL)METHYL]-2-(METHYL-AMINO)PHENOL This product forms part of the invention in the same way as Example 16, for which it constitutes a synthesis intermediate.

0.08 mol of sodium hydroxide is dissolved in 5 cm$^3$ of water, and 25 cm$^3$ of methanol and 0.01 mol of 3-methyl-6-[(4-(3-benzisothiazolyl)-1-piperazinyl)methyl]benzoxazolinone hydrochloride are then added. The mixture is heated to reflux with magnetic stirring for 2 hours. The methanol is evaporated off under reduced pressure and the residue is then dissolved in 50 cm$^3$ of water. The solution is placed in a bath of ice-cold water, 6N hydrochloric acid is added until the pH=1, and the mixture is then alkalinized with 10% aqueous potassium carbonate solution until the pH=8–9. The mixture is stirred for 30 minutes. The precipitate obtained is filtered off, washed with water until the washing liquors are neutral, dried and then recrystallized in toluene.

Molar mass: 354.47 g.mol$^{-1}$ for C$_{19}$H$_{22}$N$_4$OS

Melting point: 153–154° C.

Yield: 55%

Recrystallization solvent: toluene

Rf: 0.4 Eluent: methanol (saturated with ammonia)/chloroform (1:9)

Infrared spectrometry 3320 cm$^{-1}$ νOH and νNH

3060–2760 cm$^{-1}$ νCH 1610 cm$^{-1}$ νC=C 1590 cm$^{-1}$ νC=C

| Nuclear magnetic resonance spectrometry (300 MHz, DMSO-$d_6$) | | | | |
|---|---|---|---|---|
| δ: 2.55 ppm | complex | 4H | piperazine | |
| δ: 2.70 ppm | singlet | 3H | N—CH$_3$ | |
| δ: 3.40 ppm | complex | 6H | CH$_2$, piperazine | |
| δ: 4.70 ppm | signal | 1H | OH | exchangeable with D$_2$O |
| δ: 6.40 ppm | doublet | 1H | H$_3$ | J$_{3-4}$ = 7.50 Hz |
| δ: 6.60 ppm | doublet | 1H | H$_4$ | J$_{4-3}$ = 7.50 Hz |
| δ: 6.70 ppm | singlet | 1H | H$_7$ | |
| δ: 7.50 ppm | complex | 2H | benzisothiazole | |
| δ: 8.00 ppm | complex | 2H | benzisothiazole | |
| δ: 9.20 ppm | singlet | 1H | NH | exchangeable with D$_2$O |

Stage B: 4-METHYL-7-[(4-(3-BENZO[d]1,2-THIAZOLYL)-1-PIPERAZINYL)METHYL]-3-OXO-3,4-DIHYDRO-2H-1,4-BENZOXAZINE HYDROCHLORIDE 0.01 mol of sodium is dissolved in 40 cm$^3$ of absolute ethanol. The absolute ethanol is evaporated off, and 20 cm$^3$ of dimethyl sulfoxide and 0.01 mol of 5-[(4-(3-benzisothiazolyl)-1-piperazinyl)methyl]-2-(methylamino)phenol are then added. The mixture is stirred for 30 minutes, 0.01 mol of ethyl bromoacetate is added, and the mixture is then left at room temperature with magnetic stirring for 16 hours. It is hydrolyzed in 100 cm$^3$ of ice-cold water, and the solution is acidified with 1N hydrochloric acid until the pH=1 and then alkalinized with 10% aqueous potassium carbonate solution until the pH=8–9. The mixture is stirred for 1 hour. The precipitate is filtered off, washed with water until the washing liquors are neutral, dried and then purified on a column of silica gel with the eluent, dichloromethane/methanol (9.8: 0.2). The product is solubilized in the minimum of acetone, and 100 cm$^3$ of ether saturated with gaseous hydrochloric acid are added. The mixture is stirred for 30 minutes. The precipitate is filtered off, washed with ether, dried and then recrystallized in absolute ethanol.

Molar mass: 430.96 g.mol$^{-1}$ for C$_{21}$H$_{23}$ClN$_4$O$_2$S

Melting point: 248–250° C.

Yield: 63%

Rf: 0.6 Eluent: methanol (saturated with ammonia)/chloroform (1:9)

Infrared spectrometry

3060–2820 cm$^{-1}$ νCH

2720–2420 cm$^{-1}$ νNH$^+$
1680 cm$^{-1}$ νCO
1610 cm$^{-1}$ νC=C
1590 cm$^{-1}$ νC=C

| Nuclear magnetic resonance spectrometry (300 MHz, DMSO-d$_6$) | | | | |
|---|---|---|---|---|
| δ: 3.30 ppm | singlet | 3H | N—CH$_3$ | |
| δ: 3.50 ppm | complex | 8H | piperazine | |
| δ: 4.40 ppm | singlet | 2H | CH$_2$ | |
| δ: 4.70 ppm | singlet | 2H | H$_2$ | (benzoxazine) |
| δ: 7.25 ppm | doublet | 1H | H$_5$ | J$_{5-6}$ = 8.40 Hz |
| δ: 7.35 ppm | complex | 2H | H$_6$, H$_8$ | |
| δ: 7.60 ppm | complex | 2H | benzisothiazole | |
| δ: 8.10 ppm | complex | 2H | benzisothiazole | |
| δ: 11.30 ppm | signal | 1H | NH$^+$ | exchangeable with D$_2$O |

EXAMPLE 17

3-{2-[4-(4',4"-DIFLUOROBENZHYDRYLIDENE)-1-PIPERIDINYL]ETHYL}-6-[(4-(2-FLUOROPHENYL)-1-PIPERAZINYL)METHYL]BENZOXAZOLINONE DIHYDROCHLORIDE

Using the procedure described in Example 11, but replacing 1-(2-chloroethyl)-4-(para-fluorobenzoyl)piperidine by 1-(2-chloroethyl)-4-(4',4"-difluorobenzhydrylidene)-piperidine, the product of the title is obtained.

Using the same procedure as in Examples 1 to 17, but using the appropriate starting materials, the compounds of Examples 18 to 26 are obtained:

EXAMPLE 18

3-METHYL-6-{[4-(4-AMINOSULFONYLPHENYL)-1-PIPERAZINYL]-METHYL}BENZOXAZOLINONE HYDROCHLORIDE

EXAMPLE 19

3-METHYL-6-{[4-(4-AMINOSULFONYLPHENYL)-1-PIPERAZINYL]-METHYL}BENZOTHIAZOLINONE HYDROCHLORIDE

EXAMPLE 20

4-METHYL-7-{[4-(4-AMINOSULFONYLPHENYL)-1-PIPERAZINYL]METHYL}-3-OXO-3,4-DIHYDRO-2H-1,4-BENZOXAZINE HYDROCHLORIDE

EXAMPLE 21

3-METHYL-6-{[4-(3-METHOXYPHENYL)-1-PIPERAZINYL]METHYL}-BENZOTHIAZOLINONE HYDROCHLORIDE

Melting point: 208–210° C.

EXAMPLE 22

3-METHYL-6-{[4-(3-METHOXYPHENYL)-1-PIPERAZINYL]METHYL}-BENZOXAZOLINONE HYDROCHLORIDE

Melting point: 227–229° C.

EXAMPLE 23

4-METHYL-7-{[4-(3-METHOXYPHENYL)-1-PIPERAZINYL]METHYL}-3-OXO-3,4-DIHYDRO-2H-1,4-BENZOXAZINE HYDROCHLORIDE

Melting point: 188–190° C.

EXAMPLE 24

4-METHYL-7-{[4-(4-METHOXYPHENYL)-1-PIPERAZINYL]METHYL}-3-OXO-3,4-DIHYDRO-2H-1,4-BENZOXAZINE HYDROCHLORIDE

Melting point: 156–158° C.

EXAMPLE 25

3-METHYL-6-{[4-(4-METHOXYPHENYL)-1-PIPERAZINYL]METHYL}-BENZOTHIAZOLINONE HYDROCHLORIDE

Melting point: >260° C.

EXAMPLE 26

3-METHYL-6-{[4-(4-METHOXYPHENYL)-1-PIPERAZINYL]METHYL}-BENZOXAZOLINONE HYDROCHLORIDE

Melting point: >250° C.

Pharmacological Study of the Compounds of the Invention

EXAMPLE A

IN VITRO AFFINITY TEST FOR THE D$_4$, D$_2$, and 5-HT$_{1A}$ RECEPTORS

The in vitro affinity tests for the 5-HT$_{1A}$, D4 and D$_2$ receptors were carried out according to classical binding techniques.

The results of these studies show that the compounds of the invention possess a K$_i$ of the order of 10$^{-7}$M with respect to the 5-HT$_{1A\ and\ D2}$, receptors, equivalent to an approximately 1 00-fold lower affinity than the compounds of Application EP 478446.

The affinity for the D$_{4.4}$ receptors was determined by competitive experiments with [$^3$H]spiperone (NEN, les Ulis, France). Membranes prepared from CHO cells transfected with the human D$_{4.4}$ receptor were purchased from Receptor Biology Inc. (Md., USA). The membranes (30 μg of membrane protein) are incubated in triplicate with 0.5 nM [$^3$H]spiperone and the cold ligand in a final volume of 0.5 ml for 60 min at 25° C. The incubation buffer contains 50 nM TRIS-HCI (pH 7.4), 120 mM NaCl, 5 mM KCl, 5 mM MgCl$_2$ and 1 mM EDTA. Nonspecific binding is determined with 10 μM haloperidol. At the end of the incubation, the incubation medium is filtered through WHATMAN GF/B filters impregnated with 0.1% of polyethyleneimine and washed three times with 2 ml of cooled buffer. The radioactivity retained on the filters is determined by liquid scintillation counting. The binding isotherms are analyzed by nonlinear regression using "PRISM" software (GraphPad Software Inc., S. Diego, USA) to determine IC$_{50}$ values. The latter are converted to the dissociation constant (K$_i$) by means of the Cheng-Prusoff equation:

$$K_i = IC_{50} / \{(L/K_d) - 1\}$$

in which L is the concentration of [³H]spiperone and $K_d$ is the [3H]spiperone dissociation constant of the human $D_{4.4}$ receptor (70 pM).

For the $D_{4.4}$ receptors, the affinity $K_i$ is of the order of $10^{-8}$ –$10^{-9}$, whereas the compounds of Application EP 478446 only had an affinity of the order of $10^{-6}$M.

EXAMPLE B
DETERMINATION OF THE EFFICACY AT THE HUMAN $D_{4.4}$ RECEPTORS

The efficacy was determined by measuring the activation of G proteins by stimulating the binding of [³⁵S]GTPγS (NEN, Les Ulis, France). The membranes prepared from CHO cells transfected with the human $D_{4.4}$ receptor were purchased from Receptor Biology Inc. (Md., USA). The membranes (50 μg of membrane protein) are incubated in triplicate with 0.1 nM [³⁵S]GTPγS and the cold ligand in a final volume of 0.5 ml for 20 min at 25° C. The incubation buffer contains 20 mM HEPES (pH 7.4), 3 μM GDP, 3 mM MgCl₂ and 100 mM NaCl. At the end of the incubation, the incubation medium is filtered through WHATMAN GF/B filters impregnated with water and washed three times with 2 ml of cooled buffer. The radioactivity retained on the filters is determined by liquid scintillation counting. The binding isotherms are analyzed by nonlinear regression using 'PRISM' software (GraphPad Software Inc., S. Diego, USA) to determine $EC_{50}$ and efficacy ($E_{max}$) values. The efficacy is expressed as a percentage of the stimulation of the binding of [³⁵S]GTPγS induced by dopamine.

For the tests of antagonism, the membranes are preincubated with the antagonist at a fixed concentration of dopamine for 30 min before adding the [³⁵S]GTPγS. The $IC_{50}$ values are converted to the antagonist potency constant ($K_b$) by means of the following equation:

$$K_b = IC_{50}/\{[\text{Antagonist}]/EC_{50}]+1\}$$

in which [Antagonist] is the antagonist concentration and $EC_{50}$ is the $EC_{50}$ determined in the absence of antagonist (dopamine alone).

For Example 1, the $K_b$ is 2.39±1.10 nM.
For Example 3, the $K_b$ is 16.1±5.0 nM.

EXAMPLE C
ACUTE TOXICITY

The acute toxicity was assessed after oral administration to groups of 8 mice (26±2 grams) of a dose of 650 mg.kg⁻¹. The animals were observed at regular intervals during the first day and daily for the two weeks following the treatment.

It is apparent that most of the compounds of the invention are completely nontoxic. Most of them do not give rise to any death after administration at a dose of 650 mg.kg⁻¹, and no disorders are generally noted after administration of this dose.

PHARMACEUTICAL COMPOSITIONS

Tablets intended for the treatment of mental disorders, containing a 1 mg dose of 3-methyl -6-[(4-(2-fluorophenyl)-1-piperazinyl)methyl]benzothiazolinone hydrochloride.

Preparation formula for 1000 tablets:
3-Methyl-6-[(4-(2-fluorophenyl)-1-piperazinyl)methyl] benzoxathiazolinone
hydrochloride 1 g
Wheat starch 20 g
Corn starch 20 g
Lactose 65 g
Magnesium stearate 2 g
Silica 1 g
Hydroxypropylcellulose 2 g

We claim:
1. A compound selected from those of general formula (I):

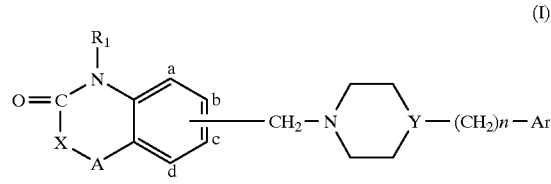

in which:

$R_1$ represents hydrogen or lower alkyl, or alternatively $R_1$ represents a group

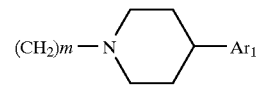

in which m is 1 to 4 inclusive to $Ar_1$ represents either CO—$Ar_2$ where $Ar_2$ represents phenyl unsubstituted or substituted with one or more radicals chosen from halogen, hydroxyl, lower alkyl, trifluoromethyl and lower alkoxy, or =C—($Ar_2$)₂ where $Ar_2$ has the same meaning as above, n represents 0 or 1
A represents oxygen or sulfur
X represents a single bond
Y represents nitrogen
Ar represents phenyl or naphthyl either in unsubstituted or substituted with one, two or three groups chosen from halogen, hydroxyl, lower alkoxy, lower alkyl, (lower alkoxy)(lower alkyl), aminosulfonyl, or Ar represents pyridyl, or 3-(benzo[d]1,2-thiazolyl) also known as 3-benzisothiazolyl:

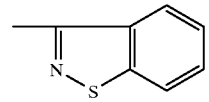

and where appropriate its isomers, pure or mixed, as well as its addition salts with a pharmaceutically-acceptable acid, or a pharmaceutically-acceptable base when $R_1$=H, on the understanding that, except where otherwise stated, the terms "lower alkyl" and "lower alkoxy" correspond to linear or branched groups having 1 to 6 carbon atoms inclusive.

2. A compound of claim 1 in which:
$R_1$ is hydrogen, methyl, or a group

for which m equals 2 and $Ar_1$ represents either a

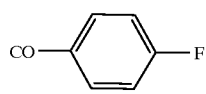

group or alternatively a

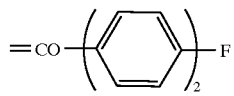

group
A is sulfur and X represents a single bond, or
A is oxygen and X represents a single bond,
the side chain is attached grafted at position c
n represents 0
Y represents nitrogen
Ar represents phenyl substituted with fluorine, chlorine, or methoxy, as well as its isomers, pure or mixed, as well as its addition salts with a pharmaceutically-acceptable acid, or a pharmaceutically-acceptable base when $R_1$=H.

3. A compound of claim 1, from selected the group consisting of:
3-methyl-6-{[4-(2-methoxyphenyl)-1-piperazinyl]methyl}benzoxazolinone, and its addition salts with a pharmaceutically-acceptable acid,
3-methyl-6-{[4-(2-methoxyphenyl)-1-piperazinyl]methyl}benzothiazolinone, and its addition salts with a pharmaceutically-acceptable acid,
3-methyl-6-{[4-(2-fluorophenyl)-1-piperazinyl]methyl}benzothiazolinone, and its addition salts with a pharmaceutically-acceptable acid,
3-methyl-6-{[4-(2-fluorophenyl)-1-piperazinyl]methyl}benzoxazolinone, and its addition salts with a pharmaceutically-acceptable acid,
3-methyl-6-{[4-(4-chlorophenyl)-1-piperazinyl]methyl}benzoxazolinone, and its addition salts with a pharmaceutically-acceptable acid,
3-methyl-6-{[4-(4-chlorophenyl)-1-piperazinyl]methyl}benzothiazolinone, and its addition salts with a pharmaceutically-acceptable acid,
6-{[4-(2-fluorophenyl)-1-piperazinyl]methyl}benzoxazolinone, and its addition salts with a pharmaceutically-acceptable acid or base,
6-{[4-(2-fluorophenyl)-1-piperazinyl]methyl}benzothiazolinone, and its addition salts with a pharmaceutically-acceptable acid or base,
3-{2-[4-(4-fluorobenzoyl)piperidyl]ethyl}-6-{[4-(2-fluorophenyl)-1-piperazin ]methyl}benzoxazolinone, and its addition salts with a pharmaceutically-acceptable acid,
3-{2-[4-(4',4"-difluorobenzhydrylidene)-1-piperidyl]ethyl}-6-{[4-(2fluorophenyl)-1-piperazinyl]methyl}benzoxazolinone, and its addition salts with a pharmaceutically-acceptable acid,
3-{2-[4-(4-fluorobenzoyl)-1-piperidyl]ethyl}-6-{[4-(2-fluorophenyl)-1-piperazinyl]methyl}, benzothiazolinone, and its addition salts with a pharmaceutically-acceptable acid,
3-methyl-6-{[4-(benzo[d][1,2]thiazolyl)-1-piperazinyl]methyl}benzoxazolinone, and its addition salts with a pharmaceutically-acceptable acid,
3-methyl-6-{[4-(benzo[d][1,2]thiazolyl)-1-piperazinyl]methyl}benzothiazolinone, and its addition salts with a pharmaceutically-acceptable acid,
3-methyl-6-{[4-(4-aminosulfonylphenyl)-1-piperazinyl]methyl}benzoxazolinone, and its addition salts with a pharmaceutically-acceptable acid,
3-methyl-6-{[4-(4-aminosulfonylphenyl)-1-piperazinyl]methyl}benzothiazolinone, and its addition salts with a pharmaceutically-acceptable acid,
3-methyl-6-{[4-(3-methoxyphenyl)-1-piperazinyl]methyl}benzoxazolinone, and its addition salts with a pharmaceutically-acceptable acid,
3-methyl-6-{[4-(4-methoxyphenyl)-1-piperazinyl]methyl}benzothiazolinone, and its addition salts with a pharmaceutically-acceptable acid,
3-methyl-6-{[4-(4-methoxyphenyl)-1-piperazinyl]methyl}benzoxazolinone, and its addition salts with a pharmaceutically-acceptable acid.

4. A compound of claim 1 which is 3-methyl-6-{[4-(2-fluorophenyl)-1-piperazinyl]methyl} benzothiazolinone or an addition salt thereof with a pharmaceutically-acceptable acid.

5. A compound of claim 1 which is 3-methyl-6-{[4-(4-chlorophenyl)-1-piperazinyl]methyl} benzoxazolinone or an its addition salt thereof with a pharmaceutically acceptable acid.

6. A method for treating a living body afflicted with a condition selected from anxiety and depression, comprising the step of administering to the living body an amount of a compound of claim 1 which is effective for alleviation of said condition.

7. A pharmaceutical composition comprising as active principle an effective amount of a compound as claimed in claim 1, together with one or more pharmaceutically-acceptable excipients or vehicles.

8. A pharmaceutical composition comprising as active principle an effective amount of a compound as claimed in claim 3, together with one or more pharmaceutically-acceptable excipients or vehicles.

9. A method for treating a living body afflicted with a condition selected from anxiety and depression, comprising the step of administering to the living body an amount of a compound of claim 3 which is effective for alleviation of said condition.

* * * * *

UNITED STATES PATENT AND TRADEMARK OFFICE
CERTIFICATE OF CORRECTION

PATENT NO. : 5,919,784

DATED : July 6, 1999

Page 1 of 3

INVENTOR(S) : D. Lesieur, P. Carato, J.P. Bonte, P. Depreux, D.H. Caignard, M. Millan, A. Newman-Tancredi, P. Renard, M.C. Rettori It is certified that error appears in the above-indentified patent and that said Letters Patent is hereby corrected as shown below:

Column 4, line 56 "3-{2[4-(4',4'-" should read
-- 3-{2[4-(4',4''- --.

Column 10, line 60: At the end of the line, "NO3" should read -- $NO_3$ --.

Column 11, line 60: "$\mu CO-O$" should read -- $vCO-O$ --.

Column 11, line 61: "$\mu C=C$" should read -- $vC=C$ --.

Column 14, line 19: "$v^{CH}$" should read -- $vCH$ --.

Column 14, line 41: "$g.mol^{31\ 1}$" should read
-- $g.mol^{-1}$ --.

Column 15, line 18 (approx.): Delete "15" at the beginning of the line.

Column 16, line 21: "Delete the word "fluoroph-" and replace with -- mol of N- --.

Column 19, line 48: In this line "4H" should read
-- 2H --.

Column 20, line 8: "$3040-2780\ cm^1\ vCH$" should read:
-- $3040-2780\ cm^{-1}\ vCH$ --.

Column 20, line 38: "$1670\ cm^1\ vCO$" should read:
-- $1670\ cm^{-1}\ vCO$ --.

UNITED STATES PATENT AND TRADEMARK OFFICE
CERTIFICATE OF CORRECTION

PATENT NO. : 5,919,784
DATED : July 6, 1999
INVENTOR(S) : D. Lesieur, P. Carato, J.P. Bonte, P. Depreux, D.H. Caignard, M. Millan, A. Newman-Tancredi, P. Renard, M.C. Rettori It is certified that error appears in the above-indentified patent and that said Letters Patent is hereby corrected as shown below:

Column 23, line 35: Delete "15" at the beginning of the line.

Column 23, line 38: "1670 cm$^1$" should read: -- 1670 cm$^{-1}$ --.

Column 23, line 46(approx): At the end of the line, "H$_4$ phenyl" should read -- H$_4$ and phenyl --.

Column 23, line 67: "100 cm$^3$Of " should read -- 100 cm$^3$ of --.

Column 25, line 39(approx.): "1760 cm$^{-1}$ vC-O" should read -- 1760 cm$^{-1}$ vCO-O --.

Column 28, line 44: "$_{and\ D2}$," should read -- and D$_2$, --.

Column 28, line 45: "1 00-fold" should read -- 100-fold --.

Column 28, line 59: "polyethyleneimine" should read -- polyethylenimine --.

Column 29, line 2: "[3H]" should read --[$^3$H] --.

Column 30, line 38(approx.): Delete the word "in".

Page 2 of 3

UNITED STATES PATENT AND TRADEMARK OFFICE
CERTIFICATE OF CORRECTION

PATENT NO. : 5,919,784
DATED : July 6, 1999
INVENTOR(S) : D. Lesieur, P. Carato, J.P. Bonte, P. Depreux, D.H. Caignard, M. Millan, A. Newman-Tancredi, P. Renard, M.C. Rettori It is certified that error appears in the above-indentified patent and that said Letters Patent is hereby corrected as shown below:

Column 30, line 43(approx.): Before the "colon" at the end of the line, insert -- of the formula --.

Column 31, line 19(approx.): Delete the word "grafted".

Column 31, line 26: "from selected" should read -- selected from --.

Column 31, line 53: "piperazin" should read -- piperazinyl] --.

Column 32, line 35: Delete the word "its"; <u>insert</u> a hyphen -- - -- between "pharmaceutically" and "acceptable".

Signed and Sealed this

Sixteenth Day of November, 1999

Q. TODD DICKINSON

Attest:

*Attesting Officer*   *Acting Commissioner of Patents and Trademarks*